(12) United States Patent
Zavras

(10) Patent No.: US 8,084,205 B2
(45) Date of Patent: *Dec. 27, 2011

(54) GENETIC RISK ASSESSMENT TECHNOLOGY FOR EPITHELIAL CANCER INVOLVING GENE-ENVIRONMENT INTERACTION BETWEEN ERCC5 AND TOBACCO USE

(75) Inventor: Athanasios I. Zavras, Dover, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 204 days.

This patent is subject to a terminal disclaimer.

(21) Appl. No.: 12/349,785

(22) Filed: Jan. 7, 2009

(65) Prior Publication Data

US 2009/0253136 A1    Oct. 8, 2009

Related U.S. Application Data

(60) Provisional application No. 61/041,695, filed on Apr. 2, 2008.

(51) Int. Cl.
*C07H 21/04* (2006.01)
*C12Q 1/68* (2006.01)

(52) U.S. Cl. ...... 435/6.1; 435/6.11; 435/6.14; 435/6.12; 536/23.1; 536/24.3

(58) Field of Classification Search ........................ None
See application file for complete search history.

(56) References Cited

U.S. PATENT DOCUMENTS

2003/0092019 A1* 5/2003 Meyer et al. ........................ 435/6

OTHER PUBLICATIONS

Jeon (Carcinogenesis, vol. 24, No. 10 pp. 1677-1681, 2003).*
Abbasi et al. (Int. J. Cancer, vol. 125, pp. 1431-1439, 2009).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Nastiuk et al (Prostates, vol. 40, No. 3, pp. 172-177, 1999).*
Cui et al. (Int. J. Cancer, vol. 118, pp. 714-720, 2006).*
Saldivar et al. (Gynecologic Oncology, vol. 107, pp. S223-S229, 2007).*
Cloud et al., "XPG protein has a structure-specific endonuclease activity," *Mut. Res.*, 347:55-60 (1995).
Coverly et al., "A role for the human single-stranded DNA binding protein HSSB/RPA in an early stage of nucleotide excision repair," *Nucl. Acids. Res.*, 20(15):3873-3880 (1992).
Divine et al., "The *XRCC1* 399 glutamine allele is a risk factor for adenocarcinoma of the lung," *Mut. Res.*, 461:273-278 (2001).
Evans et al., "Open complex formation around a lesion during nucleotide excision repair provides a structure for cleavage by human XPG protein," *EMBO J.*, 16(3):625-638 (1997).
Harfe and Jinks-Robertson, "DNA Mismatch Repair and Genetic Instability," *Annu. Rev. Genet.*, 34:359-399 (2000).
Hoeijmakers, "Genome maintenance mechanisms for preventing cancer," *Nature*, 411:366-374 (2001).
Hunting and Gowans, "DNA polymerase delta mediates excision repair in growing cells damaged with ultraviolet radiation," *Biochem. Cell, Biol.*, 69:303-308 (1991).
Khanna and Jackson, "DNA double-strand breaks: signaling repair and the cancer connection," *Nat. Gent.*, 27:247-254 (2001).
Kimball, "DNA Repair," Biology Pages: Online textbook. Accessed Jul. 15, 2007 from http://users.rcn.com/jkimball.ma.ultranet/BiologyPages/D/DNArepair.html. (2006).
Kolodner and Marsischky, "Eukaryotic DNA mismatch repair," *Curr. Opin. Genet. Dev.*, 9:86-96 (1999).
Lindahl and Wood, "Quality Control by DNA repair," *Science*, 286:1897-1905 (1999).
Mol et al., "DNA Repair Mechanisms for the Recognition and Removal of Damaged DNA Bases," *Annu. Rev. Biophys. Biomol. Struct.*, 28:101-128 (1999).
Mudgett and MacInnes, "Isolation of the Functional Human Excision Repair Gene ERCC5 by the Intercosmid Recombination," *Genomics*, 8:623-633 (1990).
O'Donovan et al., "XPG endonuclease makes the 3' incision in human DNA nucleotide excision repair," *Nature*, 371:432-435 (1994).
O'Donovan et al., "Identical defects in DNA repair in *Xeroderma pigmentosum* group G and rodent ERCC group 5," *Nature*, 363:185-188 (1993).
Petrini, "The Mre11 complex and ATM: collaborating to navigate S phase," *Curr. Opin. Cell Biol.*, 12:293-296 (2000).
Rotman and Shiloh, "ATM: from gene to function," *Hum. Molec. Genet.*, 7(10):1555-1563 (1998).
Sancar, "DNA Excision Repair," *J. Biol. Chem.*, 274:18759-18768 (1999).
Scherly et al., "Complementation of the DNA repair defect in *Xeoderma pigmentosum* group G cells by a human cDNA related to yeast RAD2," *Nature*, 363:182-185 (1993).
Wilson III and Thompson, "Life without DNA repair," *Proc. Natl. Acad. Sci. USA*, 94:12754-12757 (1997).
Zhou and Elledge, "The DNA damage response: putting checkpoints in perspective," *Nature*, 408:433-439 (2000).

* cited by examiner

*Primary Examiner* — Jeanine A Goldberg
(74) *Attorney, Agent, or Firm* — Banner & Witcoff, Ltd.

(57) ABSTRACT

Methods and compositions for assessing ERCC5 gene expression in view of certain environmental exposures and determining the risk of an individual for developing one or more epithelial cancers are provided.

36 Claims, 11 Drawing Sheets

```
GCAAATAATA CAGAAGCCAC GGTTTTCCAG TGGGGGACGG CACTAATGGG AGCGCATTAA
AGCGGAGAGA CTCTGGCTGC AACACGTCTC AGCAGCTGTC ACCGCCTCCC GGAAGAAAGA
CRGGTCCAGA GAATGGCCGT TGGCGGGGAG GGGCAGGGCC TCGCCTCGCC CAGCGCTTAG
GCCCAAACGT CTGCGCCGCT AATGGAAGAC CGGGGTGCAA GGGCCACGCA GGCGACGGAA
ACAGCCAGAA GATGTCCCTG CGACACCTCC CGCCTTCGCT GGTGGGTCCG CAAACCCA
Y
GAAAAATGGG CCCGCTCGGT TTCCGTCTAA TACGACGCGC AGGGCGGAAG CTCCGCCTCC
GCACATGACG TATATTTTCT GCGCTTGCAG CACTCCGGAA GTGAGAAGTT TAGCGCYAGT
GGTGATGCCT TGGTGGTTAC TTGCTTCCGT CACGCTGGCA TCCTGAAGGC GTTAAGCATT
AAAACAATGT GCAAAAGCGC CTTCTTGGTG GAGTAACGGG CTTTTGTTTT TGTTTGAGAC
AGGGTCTCAC GCTGTCGCCC ATACTGGAGT CCAGTGGCGC ATTCTTAGCT CACTGCAGCY
TGGAACTCCT GCTGCCCGAG CTCAAGCAAC TTTCCCATCT CAGCCTCTSA AGTAGCTGGG
ACCGCAGGTG CGCACCACTA TGCTTGGCGA ATTATTTTTG TAGAAATGAG GTCTCCCTGT
GTTGCCCAGG CTGGGAGCTA TTTTCTACAC GCTTTTTAG TATCGGTTTC TACCTTTGCG
CCGCCGTGTG TGAAGATACT TAACACAAAG
```

| 2 | 357 | 1 | 0 | 0 | 2:0 | 0 | 34 | 1 | 0 | 0 | 3 | 0 | 1 | 1 |
|---|---|---|---|---|---|---|---|---|---|---|---|---|---|---|
| 2 | 293 | 2 | 16 | 0 | 1:0 | 5 | 21 | 1 | 0 | 1 | 14 | 0 | 1 | 2 |
| 2 | 551 | 2 | 11 | 0 | 1:1 | 4 | 21 | 1 | 0 | 1 | 53 | 0 | 1 | 1 |
| | 294 | 2 | 8 | 0 | 1:0 | 5 | 28 | 1 | 0 | 2 | 21 | 0 | 1 | 1 |
| 2 | 318 | 5 | 53 | 0 | 1:1 | 0 | 26 | 1 | 0 | 2 | 3 | 0 | 1 | 1 |
| 1 | 270 | 2 | 24 | 0 | 2:1 | 3 | 26 | 1 | 1 | 0 | 54 | 0 | 1 | 1 |
| 2 | 530 | 3 | 13 | 5 | 1:1 | 0 | 22 | 1 | 0 | 1 | 13 | 0 | 1 | 1 |
| 2 | 355 | 1 | 0 | 0 | 2:0 | 0 | 24 | 1 | 0 | 3 | 14 | 0 | 1 | 2 |
| 2 | 472 | 4 | 28 | 3 | 9:1 | 0 | 24 | 1 | 1 | 1 | 15 | 0 | 1 | 1 |
| 1 | 348 | 2 | 5 | 0 | 1:0 | 5 | 21 | 1 | 0 | 3 | 3 | 0 | 1 | 2 |
| 2 | 355 | 1 | 0 | 0 | 2:0 | 0 | 23 | 1 | 0 | 0 | 12 | 0 | 1 | 1 |
| 2 | 544 | 1 | 0 | 0 | 1:1 | 0 | 28 | 1 | 1 | 1 | 14 | 0 | 1 | 1 |
| 1 | 549 | 2 | 13 | 0 | 1:1 | 5 | 20 | 1 | 0 | 3 | 18 | 0 | 1 | 2 |
| 2 | 560 | 1 | 0 | 0 | 1:0 | 0 | 22 | 1 | 1 | 1 | 3 | 0 | 1 | 1 |
| 1 | 515 | 1 | 0 | 0 | 1:0 | 0 | 26 | 1 | 0 | 10 | 6 | 0 | 1 | 2 |
| 1 | 559 | 1 | 0 | 0 | 1:0 | 0 | 25 | 1 | 1 | 4 | 7 | 0 | 1 | 1 |
| | 559 | 2 | 2 | 0 | 1:0 | 3 | 24 | 1 | 0 | 1 | 3 | 0 | 1 | 1 |
| 2 | 459 | 1 | 0 | 0 | 1:0 | 0 | 21 | 1 | 1 | 1 | 32 | 0 | 1 | 2 |
| 2 | 525 | 4 | 34 | 3 | 1:0 | 0 | 22 | 1 | 0 | 2 | 3 | 0 | 1 | 1 |
| 0 | 363 | 2 | 1 | 0 | 1:0 | 5 | 24 | 1 | 0 | 3 | 3 | 0 | 1 | 2 |
| 2 | 409 | 2 | 15 | 0 | 1:0 | 5 | 25 | 1 | 1 | 5 | 3 | 0 | 1 | 2 |
| | 546 | 1 | 0 | 0 | 1:1 | 0 | 28 | 1 | 0 | 4 | 35 | 0 | 1 | 2 |
| 2 | 435 | 2 | 16 | 0 | 1:0 | 5 | 26 | 1 | 1 | 1 | 23 | 0 | 1 | 2 |
| 1 | 278 | 1 | 0 | 0 | 1:. | 0 | 34 | 1 | 0 | 1 | 22 | 0 | 1 | 1 |
| 2 | 524 | 1 | 0 | 0 | 1:0 | 0 | 33 | 1 | 0 | 1 | 6 | 0 | 1 | 2 |
| 1 | 251 | 1 | 0 | 0 | 1:0 | 0 | 27 | 1 | 0 | 1 | 42 | 0 | 1 | 1 |
| 2 | 294 | 2 | 35 | 0 | 1:1 | 5 | 28 | 1 | 1 | 3 | 3 | 0 | 1 | 1 |
| 2 | 489 | 1 | 0 | 0 | 1:0 | 0 | 27 | 1 | 0 | 1 | 7 | 0 | 1 | 2 |
| 2 | 238 | 2 | 40 | 0 | 1:0 | 5 | 25 | 1 | 0 | 1 | 3 | 0 | 1 | 2 |
| 2 | 360 | 2 | 2 | 0 | 1:0 | 5 | 28 | 1 | 0 | 1 | 3 | 0 | 1 | 2 |
| 2 | 386 | 2 | 28 | 0 | 1:. | 3 | 31 | 1 | 0 | 1 | 13 | 0 | 1 | 2 |
| 2 | 509 | 2 | 13 | 0 | 1:1 | 5 | 23 | 1 | 1 | 1 | 17 | 0 | 1 | 2 |
| 1 | 536 | 1 | 0 | 0 | 1:0 | 0 | 22 | 1 | 0 | 2 | 3 | 0 | 1 | 1 |
| | 373 | 4 | 48 | 2 | 1:0 | 0 | 30 | 1 | 1 | 0 | 44 | 0 | 1 | 1 |
| 1 | 240 | 1 | 0 | 0 | 1:0 | 0 | 21 | 1 | 0 | 3 | 12 | 0 | 1 | 2 |
| 1 | 551 | 1 | 0 | 0 | 1:0 | 0 | 28 | 1 | 1 | 1 | 3 | 0 | 1 | 2 |

| | 561 | 2 | 10 | 0 | 1 | 5 | 25 | 1 | 1 | 0 | 0 | 0 | 1 | 1 |
| 1 | 551 | 1 | 0 | 0 | 13 | 0 | 26 | 1 | 0 | 2 | 11 | 0 | 1 | 2 |

Figure 2 Cont.

SEQUENCE LISTING

<160> NUMBER OF SEQ ID NOS: 1

<210> SEQ ID NO 1
<211> LENGTH: 809
<212> TYPE: DNA
<213> ORGANISM: Homo sapiens

<400> SEQUENCE: 1

```
gcaaataata cagaagccac ggttttccag tgggggacgg cactaatggg agcgcattaa      60
agcggagaga ctctggctgc aacacgtctc agcagctgtc accgcctccc ggaagaaaga     120
crggtccaga gaatggccgt tggcggggag gggcagggcc tcgcctcgcc cagcgcttag     180
gcccaaacgt ctgcgccgct aatggaagac cggggtgcaa gggccacgca ggcgacggaa     240
acagccagaa gatgtccctg cgacacctcc cgccttcgct ggtgggtccg caaacccayg     300
aaaaatgggc ccgctcggtt tccgtctaat acgacgcgca gggcggaagc tccgcctccg     360
cacatgacgt atattttctg cgcttgcagc actccggaag tgagaagttt agcgcyagtg     420
gtgatgcctt ggtggttact tgcttccgtc acgctggcat cctgaaggcg ttaagcatta     480
aaacaatgtg caaaagcgcc ttcttggtgg agtaacgggc ttttgttttt gtttgagaca     540
gggtctcacg ctgtcgccca tactggagtc cagtggcgca ttcttagctc actgcagcyt     600
ggaactcctg ctgcccgagc tcaagcaact ttcccatctc agcctctsaa gtagctggga     660
ccgcaggtgc gcaccactat gcttggcgaa ttattttgt agaaatgagg tctccctgtg      720
ttgcccaggc tgggagctat tttctacacg ctttttttagt atcggtttct acctttgcgc    780
cgccgtgtgt gaagatactt aacacaaag                                       809
```

GENETIC RISK ASSESSMENT TECHNOLOGY FOR EPITHELIAL CANCER INVOLVING GENE-ENVIRONMENT INTERACTION BETWEEN ERCC5 AND TOBACCO USE

RELATED APPLICATION

This application claims priority from U.S. provisional patent application No. 61/041,695, filed Apr. 2, 2008, which is hereby incorporated herein by reference in its entirety for all purposes.

STATEMENT OF GOVERNMENT INTERESTS

This invention was made with government support under National Institutes of Health grant number DE015593. The Government has certain rights in the invention.

FIELD

The present invention relates to methods and compositions useful for cancer diagnosis, prognosis, treatment and prevention.

BACKGROUND

Cancer causes a significant burden of disease around the world. In the United States, one of every three adults are expected to develop some form of cancer in their lifetime. Solid tumors are the most prevalent types of cancer. There is an unmet need in early diagnosis and prognosis of asymptomatic epithelial cancer patients. This need is particularly significant given that early diagnosis or prognosis results can significantly influence the course of disease by influencing treatment choices, thresholds and goals, and possibly enhance compliance.

Screening for epithelial cancers such as, for example, cancers of the upper aerodigestive track (oral cavity, larynx, pharynx, esophagus), stomach, lung, cervix, colon, penis, rectum or for pre-malignant lesions in the previously-mentioned sites, is a complex process that currently involves clinical, histologic and radiologic examination. Screening methods at the molecular level are needed to identify individuals that possess increased intrinsic risks for specific biologic pathways leading to premalignancies or cancer.

Equally important for the prevention or early diagnosis of epithelial cancers, risk assessment methods are needed to incorporate genomic findings to improve the prediction of a person's probability of developing the above-named cancers or premalignancies. At the population level, tobacco use is widely recognized as a major risk factor for epithelial cancer. Risk assessment methods are needed to screen large populations for increased cancer risk. Such genomic findings can have a significant impact on a person's decision to discontinue smoking. An additional area that genomic findings of genetic susceptibility can have an important impact in managing epithelial cancers is in the clinical development of novel chemotherapeutics. Targeted development according to one's unique genetic characteristics will lead to the development of the next generation of biologic therapies for cancer.

Tobacco use is a well-established risk factor or causative agent of epithelial cancers of the oral cavity, pharynx, larynx, esophagus, lung, stomach, cervix, and colon/rectum. According to the World Health Organization, tobacco use is associated with 5,000,000 deaths annually; due to a continuing trend of increased utilization globally, the number of deaths from tobacco-related diseases is expected to double in the next two decades. Therefore there is an unmet need for behavioral interventions and tobacco cessation activities that incorporate risk markers as deterrents to the initiation or continuation of tobacco products.

The human genome is continuously faced with the challenge of preserving its stability and integrity as cellular DNA is threatened by exogenous and endogenous sources. Environmental agents, such as ultraviolet light, ionizing radiation, toxic chemicals and carcinogens (e.g., those found in tobacco), and the like alter the structure of DNA leading to mutations that increase the risk of cancer. Cellular by-products of metabolism, like reactive oxygen species, are continual enemies of DNA integrity that create endogenous genetic damage. Genetic instability is further promoted by spontaneous changes in the DNA, such as deamination of cytosine which leads to the miscoding of uracil. Finally, despite the precision of the DNA machinery, errors occur in normal transcriptional processes that contribute to the overall instability.

The damage rendered from these agents results in various outcomes, most of which are adverse. Disturbances in DNA metabolism can result in cell-cycle arrest or apoptosis. Lesions may block the progress of replication, transcription, or chromosome segregation resulting in mutations or apoptosis (programmed cell death). The long term consequences of permanent mutations and chromosome aberrations include aging and cancer. Cancers and other diseases, of various types and severity, also result from inherited genetic defects.

In view of the various lesions encountered, one repair process is not sufficient to protect human DNA. As a result, evolution has created multiple, sophisticated DNA repair pathways that, collectively, protect the cell against most insults. The task of protection is divided into several primary repair pathways: direct reversal, base excision repair (BER), mismatch repair (MMR), homologous recombination and end joining, and nucleotide excision repair (NER). In the past decade, knowledge about these mechanisms has rapidly expanded regarding modality, function, and genetic etiology. To date, about 150 repair genes have been identified and described (Wood et al. (2005) *Mutat. Res.*, 577: 275-283). However, the role of DNA repair in cancer development is not fully understood. Inherited defects in several DNA repair enzymes have shown to predispose individuals to cancer development, suggesting an important relationship between these mechanisms and cancer.

NER is the most versatile of the DNA repair pathways and is found in all the different kingdoms of life, including eubacteria, archaea, and eukaryotes (Batty and Wood (1999) *Gene*, 241:193-204). In human cells, NER is responsible for repairing a multitude of lesions that distort the helix, interfere with Watson and Crick base pairing, and obstruct DNA transcription (Costa et al. (2003) *Biochimie*, 85:1083-1099). For example, two of the major helical distorting lesions targeted by NER are cyclobutane pyrimidine dimers (CPDs) and 6-4 photoproducts, both of which are induced by UV light. The human syndrome, xeroderma pigmentosum (XP), which results in severe photosensitivity and a high incidence of skin cancer, is known to be caused by NER defects. Studies of this syndrome, utilizing XP patient cells, have led to identification of the genes encoding the proteins involved in NER (Costa et al. (2003), supra). These proteins comprise seven complementation groups, identified as XPA-G.

The basic NER process involves three major steps: 1) damage recognition and assembly of the incision complex, 2) dual DNA incision and damage excision, and 3) DNA repair synthesis and ligation (Dip et al. (2004) *DNA Repair*, 3:1409-

1423). The core components of NER have been identified via cloning and the core reaction has been reconstituted. The core factors assemble into two large multi-enzyme machines: one, which recognizes DNA damage and performs the incision, and the second, which constructs the repair patch (Aboussekhra et al. (1995) *Cell*, 80:859-868; Mu et al. (1995) *J. Biol. Chem.*, 270:2415-2418; Araujo et al. (2000) *Genes Dev.*, 14:349-359; Huan et al. (1994) *Proc. Natl. Acad. Sci. U.S.A.*, 91:12213-12217).

In the first step, damage recognition, the XPC-hHR23B complex is thought to be responsible for the initial detection of DNA lesions. XPC is a 125 kDa protein product of the XPC gene that associates with hHR23B, a 58 kDa homolog of the Rad23 protein in yeast (Masutani et al. (1994) *EMBO J.*, 13:1831-1843). Centrin 2, an 18 kDa centrosome component is also found within the complex (Araki et al. (2001) *J. Biol. Chem.*, 276:18665-18672). The hHR23B subunit protects XPC from proteolytic degradation; thus, all cellular XPC protein is complexed with hHR23B (Dip et al. (2004), supra; van der Spek et al. (1996) *Nucl. Acids Res.* 24:2551-2559).

The model that XPC is the first arriving factor is still under debate as some contest that other factors, such as XPA, are responsible for the initial lesion recognition (Wakasugi and Sancar (1999) *J. Biol. Chem.*, 274:18759-18768). Recent hypotheses suggest that XPC-hHR23B does indeed act as the initial sensor, but it is not the sole factor responsible for lesion recognition (Dip et al. (2004), supra). Instead, Dip et al. suggest that NER machinery recognizes lesions via a bipartite process that involves two separate steps: recognition and proof-reading. Id. XPC identifies distortions in the DNA via interactions with bases unable to form normal hydrogen bonds, binding to them with high affinity. Id.

Once the lesion has been identified by XPC-hHR23B, TFIIH is recruited to the site via XPC's interaction with the XPB and p62 subunits (Yokoi et al. (2000) *J. Biol. Chem.*, 275:9870-9875). TFIIH is composed of a total of nine polypeptides: XPB, XPD, p62, p52, p44, p34, cdk7, cyclin H, and MATT (Drapkin and Reinberg (1994) *Trends Biochem. Sci.*, 19:504-508). TFIIH is hypothesized to complete the second step of damage recognition: proofreading (Dip et al. (2004), supra). First, TFIIH is loaded onto the damaged strand where it begins to unwind the DNA by 20-25 base pairs, utilizing two DNA helicases with complementary functions: XPD unwinds the DNA in 5'→3' direction, while XPB unwinds the DNA in the opposite direction (Weeda et al. (1990) *Cell*, 62:777-791; Weber et al. (1990) *EMBO J.*, 9:437-1447; Schaeffer et al. (1994) *EMBO J.*, 13:2388-2392; Roy et al. (1994) *Cell*, 79:1093-1101). The arrested function of one helicase and the continued translocation of the other results in distortion of the helix, which is thought to further the recruitment of other NER factors and serve as verification that damage does, indeed, exist (Dip et al. (2004), supra). Without recognition of damage, ATP hydrolysis by TFIIH will occur and the existing factors will disassociate (Costa et al. (2003), supra).

Once TFIIH is bound, the XPA-RPA complex can be incorporated into the incision complex. XPA is a 36 kDa, $Zn^{2+}$-finger protein that shows a binding affinity for damaged DNA and associates with other core NER factors (Dip et al. (2004), supra). XPA's affinity for damaged DNA led to the concept that it may be responsible for DNA recognition; however, multiple studies have shown that its affinity is lower and less selective than that of XPC, leading to the current model as previously discussed (Lao et al. (1999) *Biochemistry*, 38:3974-3984). RPA (replication protein A), composed of three subunits (70, 30, and 14 kDa), also shows an affinity for damaged DNA and is needed (as is XPA) to help TFIIH open the double helix around the lesion (Evans et al. (1997) *EMBO J.*, 16:6559-6573; Mu et al. (1997) *J. Biol. Chem.*, 272:28971-28979). The 70 kDa subunit of RPA, which possesses three DNA binding domains, is about 30 nucleotides in length; this roughly matches the gapped DNA in NER and is thought to confer protection to the undamaged DNA strand as well as recruit replication factors (Dip et al. (2004), supra; Kolpashchikov et al. (2001) *Nucl. Acids Res.*, 29:373-379). An additional function of XPA-RPA is the interaction with the two site-specific endonucleases, XPG and XPF-ERCC-1, to ensure that they incise at the correct location and the undamaged strand remains uncut (de Laat et al. (1998) *Genes Dev.*, 12:2598-2609; Matsunaga et al. (1996) *J. Biol. Chem.*, 271:11047-11050; Bessho et al. (1997) *J. Biol. Chem.*, 272: 3833-3837). RPA has been found to have an additional role in DNA synthesis, following excision, as it remains associated to the DNA substrate, as compared to the other core factors which are released (Dip et al. (2004), supra). In summary, the XPA-RPA complex is thought to double-check that the pre-incision complex design is correct-in assembly and location-prior to activation of the two endonucleases and subsequent incision. Id.

The final step in the assembly of the incision complex is the recruitment of XPG and XPF-ERCC1. XPG is thought to be recruited first, as it associates with the center of DNA damage in XPA cells, while XPF does not (Volker et al. (2001) *Mol. Cell*, 8:213-224). Interestingly, XPG is thought to already be present in the pre-incision complex, prior to XPA, due to its stabilizing interaction with TFIIH (Araujo et al. (2001) *Mol. Cell. Biol.*, 21:2281-2291). Studies utilizing cells with mutations in XPA support this hypothesis as XPG was still found to be at the damaged DNA sites (Volker et al. (2001), supra). However, in these XPA deficient cells, XPG was not able to make its 3' incision, suggesting that XPA, along with RPA, is necessary for activating the endonuclease (de Laat et al. (1998) *Nucl. Acids Res.*, 26:4146-4152). This suggests that the three factors, XPG, XPA, and RPA work together to bind to DNA (Reardon and Sancar (2003) *Genes Dev.*, 17:2539-2551; Riedl et al. (2003) *EMBO J.*, 22:5293-5303).

The XPG gene encodes a structure-specific 3' endonuclease that 45 cleaves substrates containing bubbles, stem-loops, and splayed arms 46-50 as well as single strand overhangs from duplex DNA (Habraken et al. (1995) *J. Biol. Chem.*, 270:30194-30198). Incisions are always made in one strand of duplex DNA, at the 3' boundary of the open DNA complex. In NER, the XPG-encoded endonuclease has an additional function, an architectural one, as it is also required for the formation of the complete open complex (Evans et al. (1997), supra; Mu et al. (1997), supra).

The XPF-ERCC1 complex is the last factor incorporated into the incision complex (Volker et al. (2001), supra; Wakasugi and Sancar (1998) *Proc. Natl. Acad. Sci. U.S.A.*, 95:6669-6674; Mu et al. (1996) *J. Biol. Chem.*, 271:8285-8294). XPF-ERCC1 encodes a structure-specific 5' endonuclease that cleaves similar lesions to the 3' endonuclease (Bessho et al. (1997), supra; Sijbers et al. (1996) *Cell*, 86:811-822; de Laat et al. (1998) *J. Biol. Chem.*, 273:7835-7842). Additionally, this endonuclease has been shown to participate in recombination repair; it is needed to cleave non-homologous 3' DNA tails protruding from heteroduplex intermediates (Dip et al. (2004), supra; Adair et al. (2000) *EMBO J.*, 19:3771-3778). The XPF subunit is responsible for the incising function as it contains a conserved nuclease motif, while the ERCC-1 subunit acts to stabilize XPF and interacts with XPA, linking the heterodimer to the NER complex (Matsunaga et al. (1996), supra; Wakasugi et al. (1997) *J. Biol. Chem.*, 272: 6030-16034).

Once the incision complex is complete, incision and removal of the damaged DNA (the second step in NER), may occur. In vitro experiments have suggested that the catalytic activity of the endonucleases is inhibited by TFIIH, in the absence of ATP; the addition of ATP reverses this inhibition, allowing incision to occur (Costa et al. (2003), supra). The 3' endonuclease incision occurs first, followed by the 5' endonuclease. XPG activity can continue in the absence of XPF-ERCC1, but XPF-ERCC1, although its catalytic activity does not rely on prior XPG-mediated incision, does require the presence of the XPG protein in the incision complex (Mu et al. (1997), supra; Wakasugi et al. (1997), supra). The incisions occur asymmetrically around the lesion, with the 3' incision three to nine nucleotides away from the lesion and the 5' incision 15-25 nucleotides away from the lesion (Dip et al. (2004), supra).

The excised oligonucleotide, containing 24-32 nucleotides, is released, leaving a hydroxyl group at the 3' end of the gap; this signifies the end of the second step. Without intending to be bound by scientific theory, at this point in time, most of the NER proteins have likely begun to disassemble and leave as the machinery for synthesis arrives. One core factor, RPA, remains at the site as it provides the template strand with protection from nucleases. The two DNA polymerases identified in the synthesis process are DNA Pol α and DNA Pol δ. PCNA and replication factor C (RFC), both proteins that act as processivity factors, are also required for DNA synthesis (Shivji et al. (1992) *Cell,* 69:367-374). In vitro synthesis utilizing these five factors (RPA, DNA Pol α or DNA pol δ, PCNA, and RFC) has been successful (Shivji et al. (1995) *Biochemistry,* 34:5011-5017). Finally, ligation of the 5' end of the newly synthesized DNA to the original sequence occurs, it seems, via DNA ligase I.

It is important to note that cells possess a more efficient repair pathway termed transcription coupled repair (TCR). In the 1980's, it was observed that NER proceeds at a much quicker rate in actively transcribed mammalian genes than in transcriptionally silent genes (Friedberg (1996) *Annu. Rev. Biochem.,* 65:15-42; Hanawalt (1994) *Science,* 266:1957-1958; Hanawalt and Spivak (1999) *Advances in DNA Repair* (eds. Dizdaroglu and Karakaya) Academic/Plenum Publishing, New York, pp. 169-179). The transcribed strand, specifically, is repaired at a much faster rate than the un-transcribed stand (Friedberg (1996), supra; Hanawalt (1994), supra; Hanawalt and Spivak (1999), supra). TCR is designated as one of two sub-pathways of NER; the other sub-pathway, global genome repair (GGR) was described in the previous paragraphs. Unlike GGR, XPC-hHR23B is not necessary in TCR (Batty and Wood (1999), supra). Instead, it is thought that the arrested RNA polymerase II recognizes damaged DNA as the initial sensor in TCR (Friedberg (2001) *Nature,* 1:22-33). TCR is essential for re-starting the RNA synthesis process, and in doing so, protects the cell from transcription blocking lesions that may result in apoptosis (Proietti et al. (2002) *DNA Repair,* 1:209-223).

Three syndromes are known to be caused by inherited defects in NER: xeroderma pigmentosum, Cockayne syndrome, and trichothiodystrophy (TTD). All three of these disorders are characterized by intense sun sensitivity (Bootsma et al. (2001) *The Metabolic and Molecular Basis of Inherited Disease* (eds. Scriver et al.), McGraw-Hill, New York, 1:677-703; Lehmann (2001) *Genes Dev.,* 15:15-23). Persons with xeroderma pigmentosum experience a high incidence of UV light induced skin cancer, neurological problems, and internal tumors (Wood et al. (2001) *Science,* 291 (5507):1284). This disorder may be the result of a mutation in any one of the seven XP genes: A-G. Cockayne Syndrome is the result of CSA or CSB gene mutations in the TCR pathway. This disorder is not associated with an increased risk for cancer and is characterized by impaired development (physical and neurological), which results in dwarfism and dysmyelination and premature aging. A combined xeroderma pigmentosum/Cockayne syndrome also exists and is thought to be the result of XPB, XBD, or XPG mutations (Lehmann (2001), supra; Friedberg et al. (1995) *DNA Repair and Mutagenesis.* (ASM Press, Washington; Bootsma et al. (1998) *The Genetic Basis of Human Cancer* (eds. Vogelstein and Kinzler) McGraw-Hill, New York pp. 245-274; Hoeijmakers (1994) *Eur. J. Cancer,* 30A:1912-1921; Rapin et al. (2000) *Neurology,* 55:1442-1449; Berneburg and Lehmann (2001) *Adv. Genet.,* 43: 71-102). TTD is very similar to Cockayne Syndrome, but is accompanied by additional symptoms like scaly skin, and brittle hair and nails. Genetic analysis has revealed that XPD genes are defective in most cases, although XPB has also been shown to cause TTD (Weeda et al. (1997) *Am. J. Hum. Genet.,* 60:320-329).

To date, the mechanisms of NER have been derived from studies that evaluate the pathway as it occurs on DNA substrates. Although this has been an incredible tool, enabling the core factors and reaction to be reconstituted, it does not represent the DNA as it exists in living cell and thus, our understanding of how NER functions in chromatin is limited (Reed (2005) *DNA Repair,* 4:909-918). Recent studies have attempted to gain insight about this aspect of NER, but they have provided only glimpses of information, setting the stage for future research.

SUMMARY

The present invention is based in part on the discovery of a significant gene-environment interaction between a gene involved in the DNA repair pathway and environmental exposure has a direct use in clinical and/or population programs for the prevention of tobacco use or its discontinuation as well as for the identification and/or treatment of epithelial cancers and/or pre-malignant lesions. In particular, the present invention is based in part on the discovery that ERCC5 variants such as, e.g., the novel rs751402 single nucleotide polymorphism of ERCC5 (a C/T polymorphism at position 298 of SEQ ID NO:1) is involved in a gene-environment interaction with tobacco use in subjects with epithelial premalignancies or cancer. This important discovery is a novel finding with direct clinical applications. For example, the polymorphism and gene environment interaction between ERCC5 and tobacco use are directly useful as targets for the design of diagnostic reagents and the development of therapeutic agents for use in the diagnosis and treatment of epithelial cancer and related pathologies.

In certain exemplary embodiments, a method of diagnosing epithelial cancer (e.g., one or more of oral cancer, laryngeal cancer, pharyngeal cancer, esophageal cancer, stomach cancer, lung cancer, cervical cancer, penile cancer, colon cancer and rectal cancer) in an individual is provided. The method includes the steps of obtaining a biological sample from an individual, detecting whether an ERCC5 variant is present in the biological sample, and diagnosing the individual with epithelial cancer if the ERCC5 variant is present in the biological sample. In certain aspects, the biological sample is one or more of a fluid sample, a tissue sample and a biopsy sample. In other aspects, the biological sample is one or more of blood, cheek cells and saliva. In certain aspects, the individual drinks alcohol, smokes tobacco and/or chews tobacco. In certain aspects, the ERCC5 variant is an ERCC5 single nucleotide polymorphism (e.g., SEQ ID NO:1 having a T at position 298).

In certain exemplary embodiments, method of diagnosing an epithelial premalignancy (e.g., one or more of oral premalignancy, laryngeal premalignancy, pharyngeal premalignancy, esophageal premalignancy, stomach premalignancy, lung premalignancy, cervical premalignancy, penile premalignancy, colon premalignancy and rectal premalignancy) in an individual is provided. The method includes the steps of obtaining a biological sample from an individual, detecting whether an ERCC5 variant is present in the biological sample, and diagnosing the individual with an epithelial premalignancy if the ERCC5 variant is present in the biological sample. In certain aspects, the biological sample is one or more of a fluid sample, a tissue sample and a biopsy sample. In other aspects, the biological sample is one or more of blood, cheek cells and saliva. In certain aspects, the individual drinks alcohol, smokes tobacco and/or chews tobacco. In certain aspects, the ERCC5 variant is an ERCC5 single nucleotide polymorphism (e.g., SEQ ID NO:1 having a T at position 298).

In certain exemplary embodiments, a method of identifying an individual at risk for developing an epithelial cancer (e.g., one or more of oral cancer, laryngeal cancer, pharyngeal cancer, esophageal cancer, stomach cancer, lung cancer, cervical cancer, penile cancer, colon cancer and rectal cancer) is provided. The method includes the steps of obtaining a biological sample from an individual, detecting whether an ERCC5 variant is present in the biological sample, and identifying the individual as being at risk for developing epithelial cancer if the ERCC5 variant is present in the biological sample. In certain aspects, the biological sample is one or more of a fluid sample, a tissue sample and a biopsy sample. In other aspects, the biological sample is one or more of blood, cheek cells and saliva. In certain aspects, the individual drinks alcohol, smokes tobacco and/or chews tobacco. In certain aspects, the ERCC5 variant is an ERCC5 single nucleotide polymorphism (e.g., SEQ ID NO:1 having a T at position 298).

In certain exemplary embodiments, method for prognosing epithelial cancer in an individual is provided. The method includes the steps of obtaining a biological sample from an individual, detecting whether an ERCC5 variant is present in the biological sample, and correlating the presence of an ERCC5 variant with an indication of an unfavorable prognosis. In certain aspects, the individual drinks alcohol, smokes tobacco or chews tobacco. In certain aspects, a favorable prognosis is made if the individual ceases smoking tobacco, chewing tobacco, and/or drinking alcohol. In certain aspects, the biological sample is one or more of a fluid sample, a tissue sample and a biopsy sample. In other aspects, the biological sample is one or more of blood, cheek cells and saliva. In certain aspects, the individual drinks alcohol, smokes tobacco and/or chews tobacco. In certain aspects, the ERCC5 variant is an ERCC5 single nucleotide polymorphism (e.g., SEQ ID NO:1 having a T at position 298).

In certain exemplary embodiments, a method of detecting epithelial cancer in a biological sample is provided. The method includes the steps of obtaining a biological sample and detecting whether an ERCC5 variant is present in the biological sample, wherein the biological sample contains epithelial cancer if the ERCC5 variant is present.

In certain exemplary embodiments, a method of detecting an epithelial premalignancy in biological sample is provided. The method includes the steps of obtaining a biological sample and detecting whether an ERCC5 variant is present in the biological sample, wherein the biological sample contains an epithelial premalignancy if the ERCC5 variant is present.

In certain exemplary embodiments, a method of screening an individual at risk for developing an epithelial cancer is provided. The method includes the steps of obtaining a biological sample from an individual, identifying the ERCC5 genotype of the individual, obtaining tobacco exposure information for the individual, and determining the individual is at risk for developing an epithelial cancer if the individual has a T at position 298 of SEQ ID NO:1 and if the individual is exposed to tobacco.

In certain exemplary embodiments, an isolated nucleic acid sequence comprising SEQ ID NO:1 having a T at position 298 is provided. In certain aspects, a polypeptide encoded by an isolated nucleic acid sequence comprising SEQ ID NO:1 having a T at position 298 is provided.

BRIEF DESCRIPTION OF THE DRAWINGS

FIG. 1 depicts the ERCC5 gene FASTA sequence from the dbSNP database (rs751402). The sequence is set forth as SEQ ID NO:1. A single nucleotide polymorphism of C/T is present at position 298. A complete list of SNPs can be accessed at the NCBI Website (ncbi.nlm.nih.gov/sites/entrez).

Figure 2:
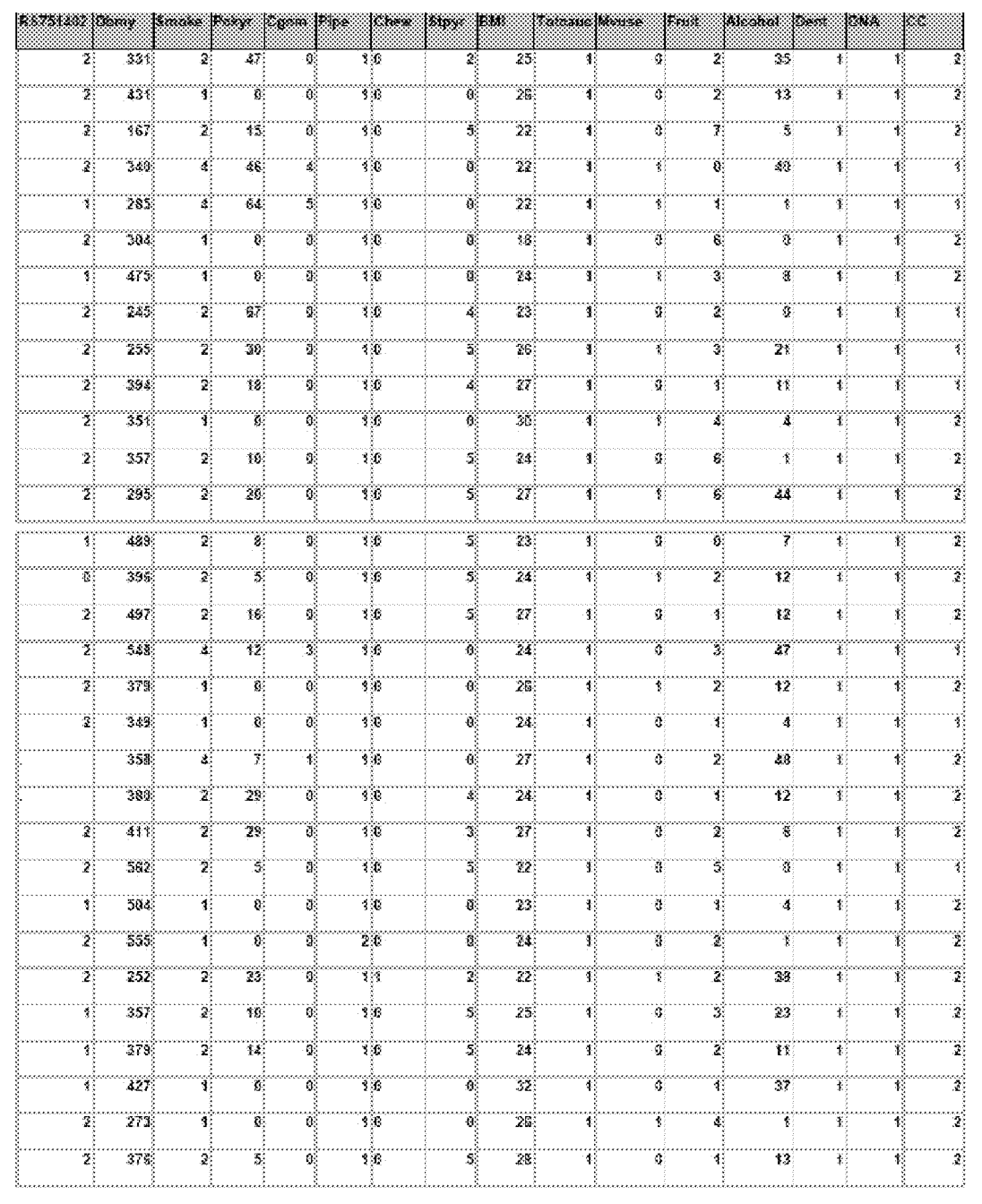
Figure 2:
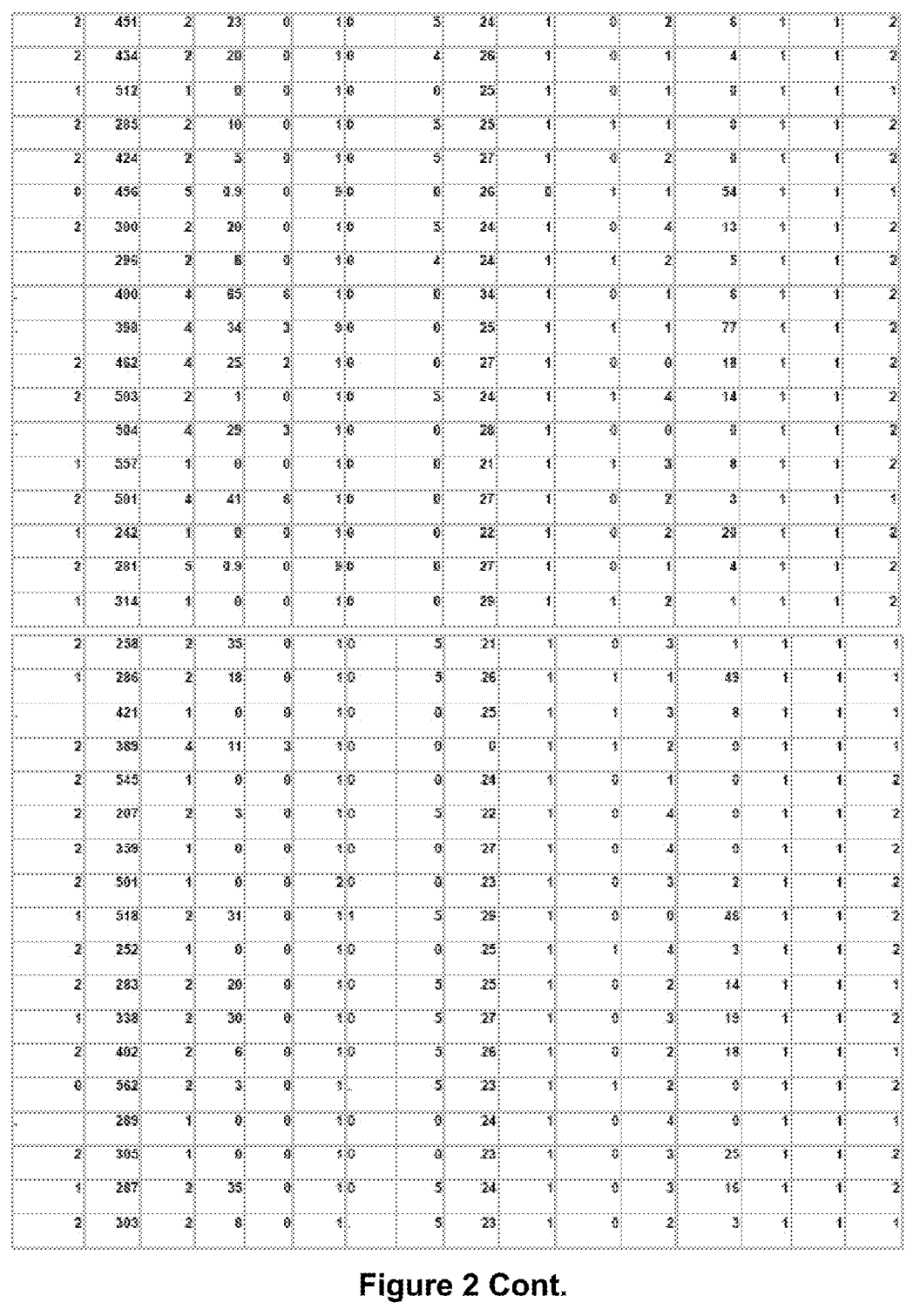
Figure 2:
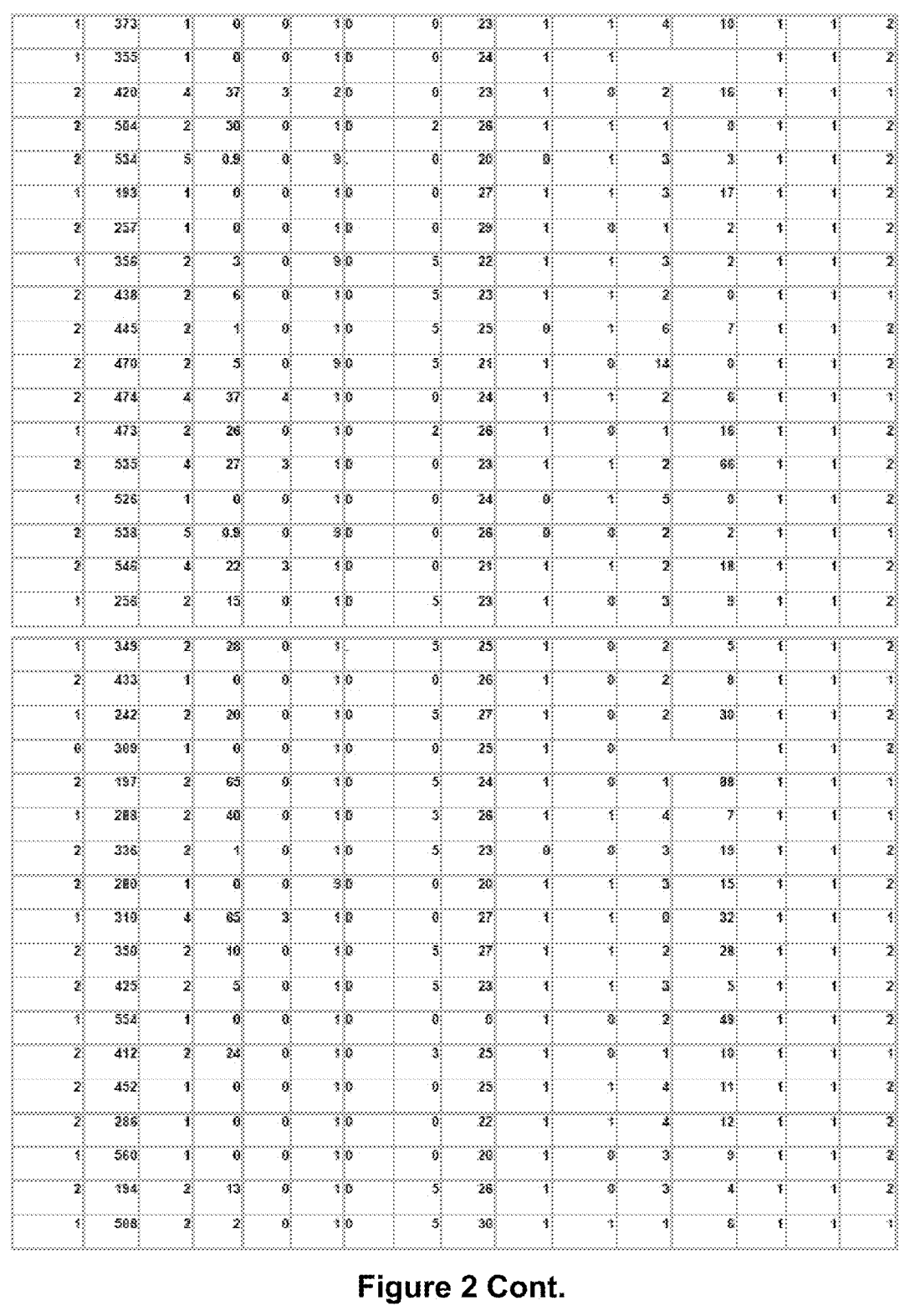
Figure 2:
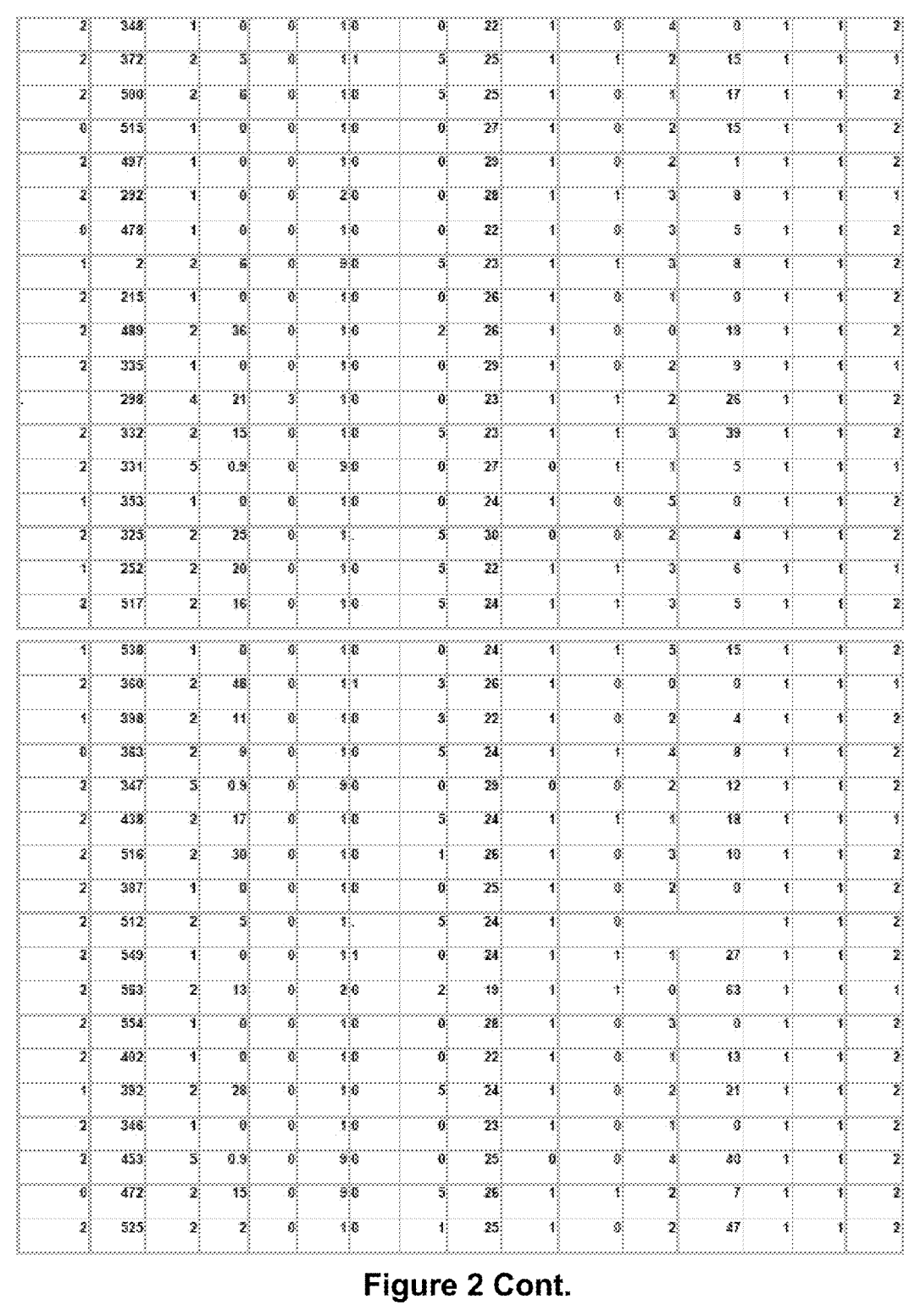
Figure 2:
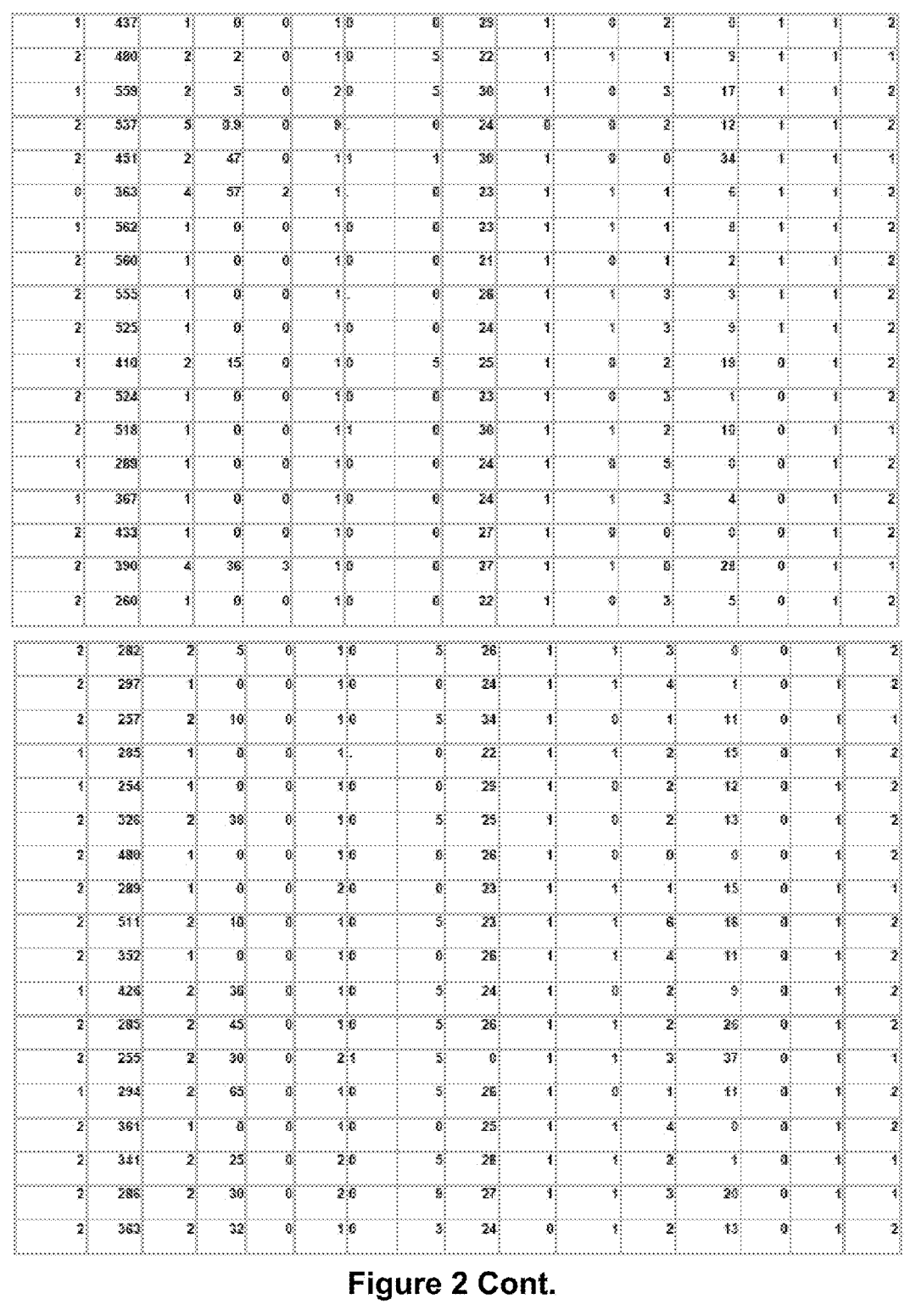
Figure 2:
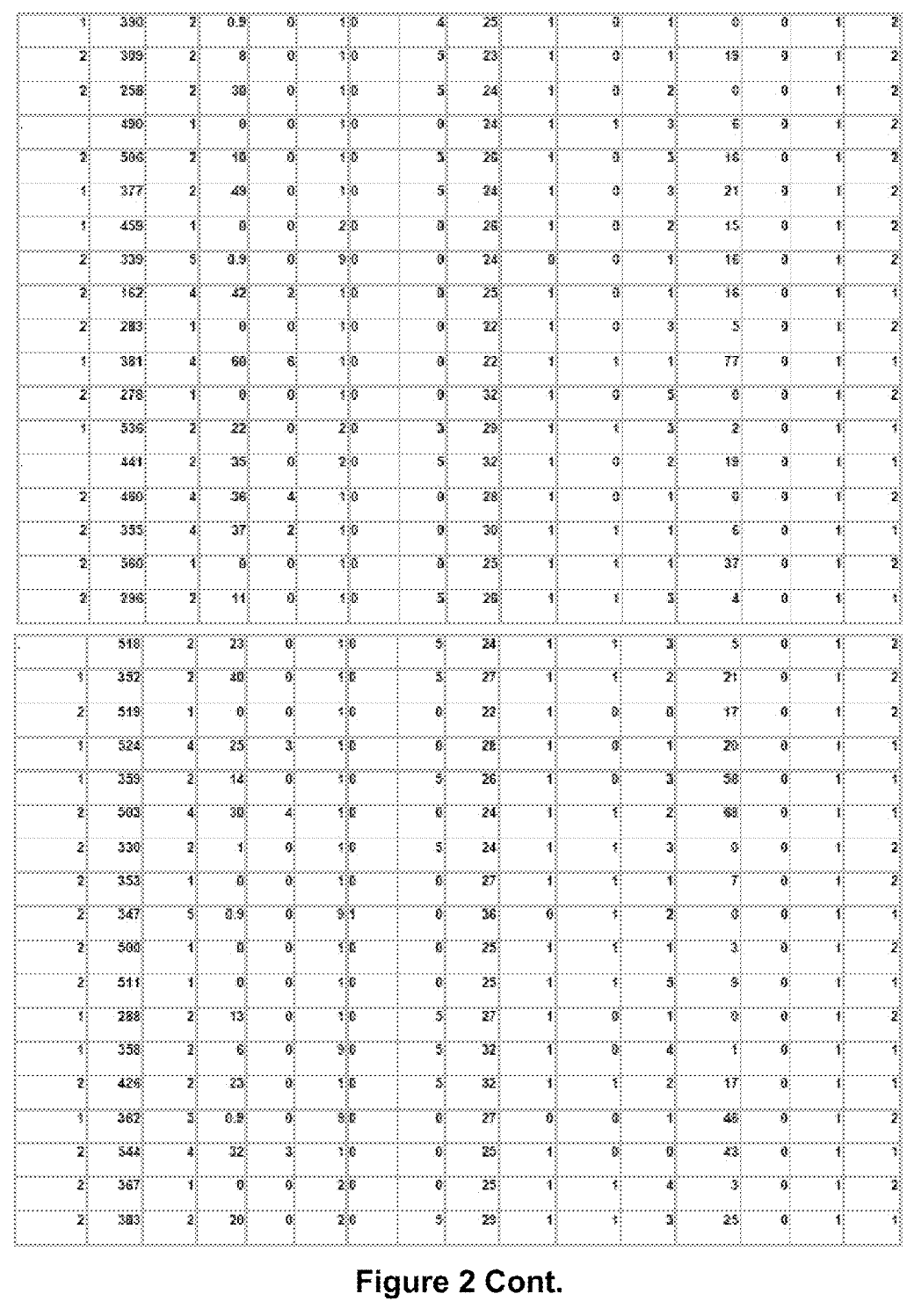
Figure 2:
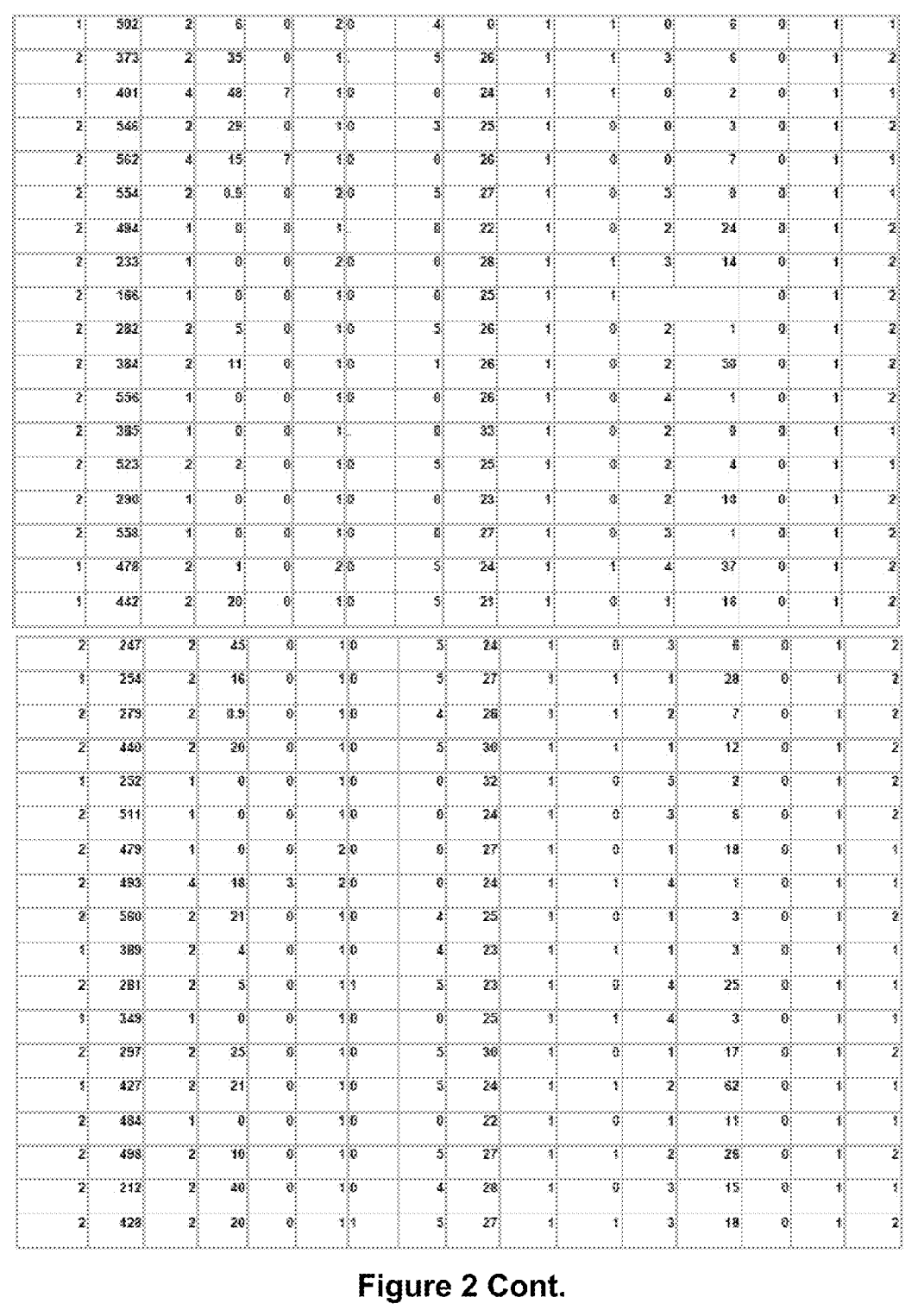
Figure 2:
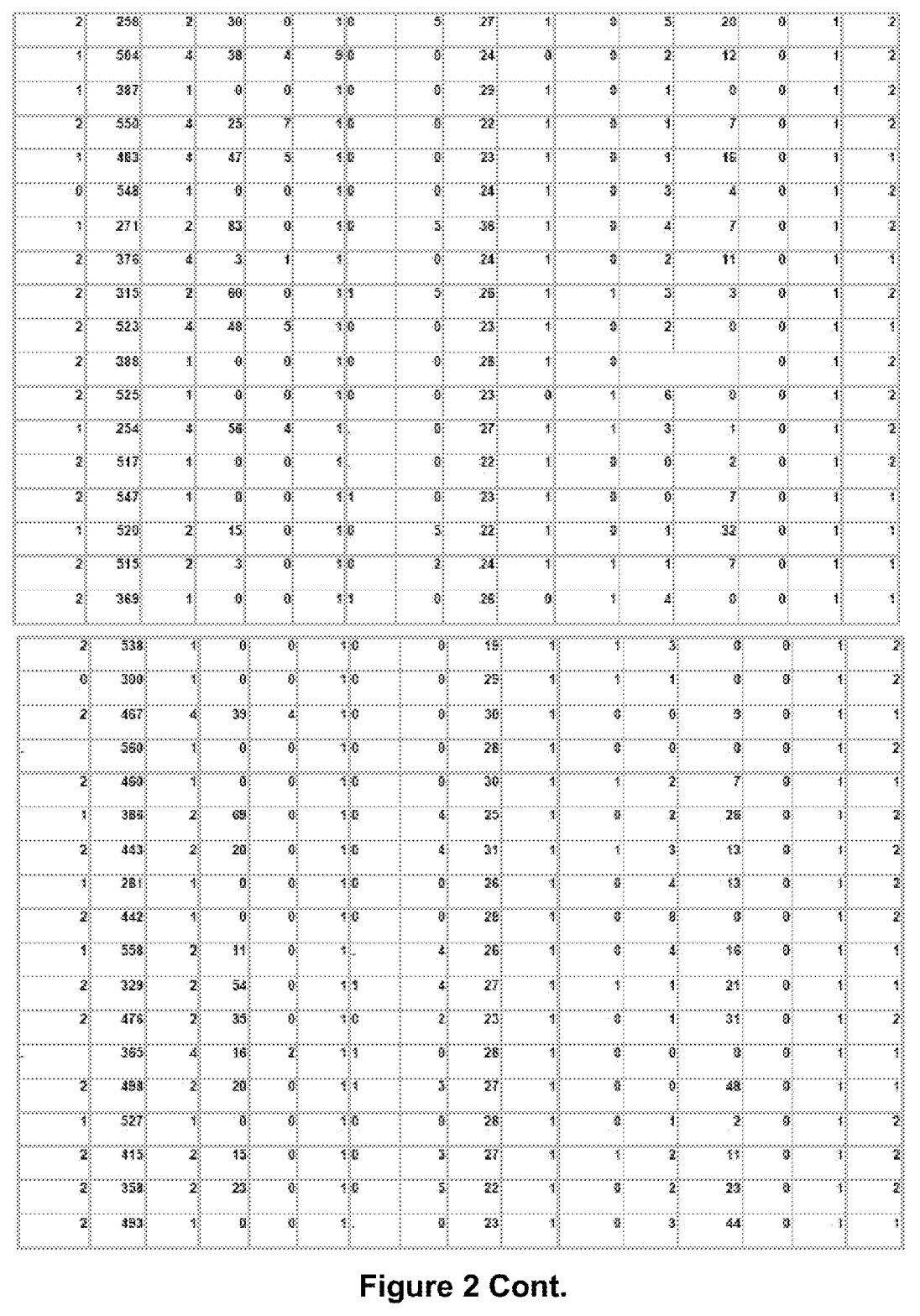

FIG. 2 depicts a table showing individual results for the ERCC5 SNP, phenotypic profile and risk factor characteristics. Each line represents data for a single individual.

DETAILED DESCRIPTION

In certain exemplary embodiments, methods and compositions for assessing the genetic risk of an individual and/or population by assessing a gene-environment interaction (e.g., an ERCC5-environment (e.g., tobacco exposure, alcohol exposure and the like) interaction). Gene-environment interactions are described further herein. In certain aspects, one of skill in the art obtains a nucleic acid sample, obtains phenotype information, and/or obtains risk factor(s) information (e.g., for tobacco and/or alcohol use; processes the sample using genotyping methods described further herein; identifies the genotype of the individual; and uses this information for a variety of applications. Applications include, but are not limited to: screening assays (e.g., to test individuals for ERCC5 SNP status); obtaining a component of complex screening assays; as a risk assessment algorithm to identify individuals at higher risk for developing cancer if they use tobacco; as part of computer algorithm(s) to be applied in prevention programs for tobacco use cessation; the development of ERCC5-specific compounds for treating cancer (e.g., compounds that inhibit ERCC5 gene and/or polypeptides, compounds that inhibit or stimulate one or more ERCC5 pathway members, anti-ERCC5 antibody(ies), anti-ERCC5 pathway member antibodies and the like).

As used herein, ERCC5 refers to the excision repair cross-complementing rodent repair deficiency, complementation group 5 (xeroderma pigmentosum, complementation group G) (ERCC5, Accession Number (human) X71342), which is involved in excision repair of UV-induced DNA damage. Mutations in humans cause Cockayne syndrome, which is characterized by severe growth defects, mental retardation, and cachexia. The XPG gene is located on chromosome 13, specifically mapping to 13q32.3-q33.177. It is about 32 kb long (31,151 bases) and contains 15 exons that range from 61 to 1074 basepairs and 14 introns that range from 250 to 5763 basepairs. To date, 282 SNPs have been identified in the ERCC5 gene. ERCC5 is also known as COFS3, ERCM2, UVDR, XPG, XPGC, Xpg, and these names are used interchangeably herein.

The gene encodes a protein, a member of the Fen1 protein family, comprised of 1186 amino acids with a molecular mass of 133 kDa. XPG is a structure-specific 3' endonuclease that cleaves damaged DNA in NER, it fulfills an architectural role as it is necessary to form an open complex around the damaged DNA, and this protein is thought to play a role in TCR. Without intending to be bound by scientific theory, any non-functional variant of ERCC5 might lead to declines in the body's natural ability to repair DNA damage due to carcinogen accumulation and the formation of DNA adducts. As used herein, the term "ERCC5 pathway member" includes the genes and polypeptides of the NER pathway, including, but not limited to, the Fen1 protein family (See, e.g., David et al. (1998) *J. Cell Biol.*, 143(5):1167-82; Oh et al. (1997) *J. Biol. Chem.*, 272:17376; Abe et al. (2001) *J. Biol. Chem.*, 276:26923; Chung et al. (2003). *J. Biol. Chem.*, 278:28872).

ERCC5 orthologs have been identified in seventeen species: *Rattus norvegicus* (RGD accession number: 1586176); *Mus musculus* (MGI accession number: 103582); *Canis familiaris* (NCBI accession numbers: XM542659.2; XP542659.2); *Pan troglodytes* (NCBI accession numbers: XM509723.2; XP509723.2); *Gallus gallus* (NCBI accession numbers: NM001034823.1; NP001029995.1); *Danio rerio* (NCBI accession numbers: NM001014315.1; NP001014337.1); *Drosophila melanogaster* (NCBI accession numbers: NM001032060.1; NP001027231.1); Saccharomyces cerevisiae (NCBI accession number: NP011774.1); *Xenopus laevis* (NCBI accession number: X69977.1); *Anopheles gambiae* (NCBI accession numbers: XM319693.2; XP319693.2); *Arabidopsis thaliana* (NCBI accession numbers: NM113721.1; NP566830.1); *Magnaporthe grisea* (NCBI accession numbers: XM369089.1; XP369089.1); *Oryza sativa* (NCBI accession numbers: NM001055848.1; NP001049313.1); *Neurospora crassa* (NCBI accession numbers: XM327783.1; XP327784.1); *Schizosaccharomyces pombe* (NCBI accession numbers: NP596095.1); *Ashbya gossypii* (NCBI accession numbers: NM211034.1; NP985680.1); and *Kluyveromyces lactis* (NCBI accession numbers: XM451412.1; XP451412.1).

In certain exemplary embodiments, ERCC5 polypeptides and nucleic acids as well as ERCC5 variants are provided. As used herein, the term "variant" is intended to include, but is not limited to, single nucleotide polymorphisms (SNPs), mutants (e.g., single mutations, double mutations, deletions, insertions and any combinations thereof) and the like.

As used herein, the term "SNP" refers to single base differences in specific position of a gene that are exhibited in various frequencies within or between different populations. SNPs comprise the great majority (over 90%) of all types of genetic variation. The SNP position is typically preceded by and followed by highly conserved sequences of the allele. An individual may be homozygous or heterozygous for an allele at each SNP position.

As used herein, the term "causative SNP" refers to a SNP that are directly and independently is predictive of a clinical phenotype. Some SNPs that are not causative SNPs nevertheless are in close association with a disease-causing sequence. In this situation, the presence of a SNP correlates with the presence of, or predisposition to, or an increased risk in developing the disease. These SNPs, although not causative, are nonetheless also useful for diagnostics, disease predisposition screening, and other uses.

Other SNPs are highly correlated with a behavioral characteristic or habit or environmental exposure, and together the SNP and the exposure may be associated with significantly higher disease incidence or prevalence. This phenomenon is used herein as a "gene-environment interaction." The combination of SNP presence and environmental exposure (e.g., to tobacco) are useful for diagnosing one or more diseases and/or disorders, screening for a predisposition to one or more diseases and/or disorders, treating one or more diseases and/or disorders, and other uses that are described further herein.

In certain exemplary embodiments, an association study of a gene environment interaction or a SNP and a specific disorder involves determining the presence or frequency of the SNP allele in biological samples from individuals with the disorder of interest, such as epithelial cancer, as well as the presence of the exposure of interest, such as tobacco use, and comparing the information to that of controls (i.e., individuals who do not have the disorder; controls may be also referred to as "healthy" or "normal" individuals) who are, in certain aspects, of similar age.

As used herein, the term "cancer" refers to various types of malignant neoplasms, most of which can invade surrounding tissues, and may metastasize to different sites (see, for example, *PDR Medical Dictionary*, 1st edition (1995), incorporated herein by reference in its entirety for all purposes). The terms "neoplasm" and "tumor" refer to an abnormal tissue that grows by cellular proliferation more rapidly than normal and continues to grow after the stimuli that initiated proliferation is removed. Id. Such abnormal tissue shows partial or complete lack of structural organization and functional coordination with the normal tissue which may be either benign (i.e., benign tumor) or malignant (i.e., malignant tumor). As used herein, the term "premaliginancy" refers to abnormal cells or tissue that are in the process of becoming malignant (e.g., precancerous lesions such as, for example, leukoplakias, erythroplakias, mixed lesions and the like).

Examples of general categories of cancer include, but are not limited to, carcinomas (i.e., malignant tumors derived from epithelial cells such as, for example, cancers of the upper aerodigestive tract (e.g., oral cavity, larynx, pharynx, esophagus and the like), stomach, lung, cervix, colon, rectum, breast, penis, prostate and the like), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells; in adults, germ cell tumors are most often found in the testicle or ovary; in fetuses, babies and young children, germ cell tumors are most often found on the body midline, particularly at the tip of the tailbone), blastic tumors (i.e., a typically malignant tumor which resembles an immature or embryonic tissue) and the like.

Examples of the types of neoplasms and/or premalignancies intended to be encompassed by the present invention include but are not limited to those neoplasms and/or premalignancies associated with epithelial cancers of the upper aerodigestive tract (e.g., oral cavity, larynx, pharynx, esophagus and the like), stomach, lung, cervix, penis, colon and/or rectum.

In certain exemplary embodiments, ERCC5 or ERCC5 variant polypeptides, nucleic acids, and modulators thereof can be used to modulate aberrant cellular proliferation and/or formation of premalignancies. In one aspect, a method for preventing in a subject, a disease or condition associated with an aberrant expression or activity of ERCC5 or ERCC5 variant, by administering to the subject an agent that modulates expression or at least one activity of ERCC5 or ERCC5 variant is provided. Subjects at risk for a disease that is caused or contributed to by aberrant expression or activity of an ERCC5 or ERCC5 variant can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. The prophylactic agents described herein, for example, can be used to treat a subject at risk of developing disorders aberrant epithelial cell proliferation and/or the development of epithelial premalignancies. For example, an antagonist of an ERCC5 variant polypeptide may be used to modulate or treat epithelial cancer (e.g., oral cancer). The appropriate agent can be determined based on screening assays described herein.

An exemplary method for detecting the presence or absence of a polypeptide or nucleic acid corresponding to an ERCC5 pathway member (e.g., ERCC5 or an ERCC5 variant) in a biological sample involves obtaining a biological sample (e.g., an epithelial cell sample and/or an epithelial cancer sample) from a test subject and contacting the biological sample with a compound or an agent capable of detecting the polypeptide or nucleic acid (e.g., mRNA, genomic DNA, or cDNA). The detection methods described herein can thus be used to detect mRNA, protein, cDNA or genomic DNA, for example, in a biological sample in vitro as well as in vivo. For example, in vitro techniques for detection of mRNA include Northern hybridizations and in situ hybridizations. In vitro techniques for detection of a polypeptide corresponding to a marker of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide corresponding to an ERCC5 pathway member (e.g., ERCC5 or an ERCC5 variant) include introducing into a subject a labeled antibody directed against the polypeptide. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker (e.g., an ERCC5 pathway member) or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker (e.g., an ERCC5 pathway member), can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In certain exemplary embodiments, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, U.S. Pat. Nos. 5,631,169 and 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor.' Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time biomolecular interaction analysis (BIA) (see, e.g., Sjolander and Urbaniczky (1991) *Anal. Chem.*, 63:2338 and Szabo et al. (1995) *Curr. Opin. Struct. Biol.*, 5:699). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas and Minton (1993) *Trends Biochem. Sci.*, 18:284). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard (1998) *J. Mol. Recognit.*, 11:141; Hage and Tweed (1997) *J. Chromatogr. Biomed. Sci. Appl.*, 699:499). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically used. Appropriate conditions to the particular assay and components thereof will be well known to one skilled in the art.

In certain exemplary embodiments, the level of mRNA corresponding to the marker (e.g., an ERCC5 pathway member (ERCC5 or an ERCC5 variant)) can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from epithelial cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of U.S. Pat. No. 4,843,155).

The isolated mRNA can be used in hybridization or amplification assays that include, but are not limited to, Southern or Northern analyses, polymerase chain reaction analyses and probe arrays. In certain exemplary embodiments, a diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question (e.g., an ERCC5 pathway member (e.g., ERCC5 or an ERCC5 variant)) is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by rtPCR (the experimental embodiment set forth in U.S. Pat. No. 4,683,202), ligase chain reaction (Barany (1991) *Proc. Natl. Acad. Sci. USA*, 88:189), self sustained sequence replication (Guatelli et al. (1990) *Proc. Natl. Acad. Sci. USA*, 87:1874), transcriptional amplification system (Kwoh et al. (1989) *Proc. Natl. Acad. Sci. USA*, 86:1173), Q-Beta Replicase (Lizardi et al. (1988) *Bio/Technology*, 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-cancer sample, or between samples from different sources.

Alternatively, the expression level can be provided as a relative expression level. To determine a relative expression level of a marker, the level of expression of the marker is determined for 10 or more samples of normal versus cancer cell isolates or 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

In certain exemplary embodiments, a polypeptide corresponding to a marker (e.g., an ERCC5 pathway member (e.g., ERCC5 or an ERCC5 variant)) is detected. In certain exemplary embodiments, an agent for detecting a polypeptide of the invention is an antibody capable of binding to a polypeptide corresponding to a marker (e.g., an ERCC5 pathway member (e.g., ERCC5 or an ERCC5 variant)) of the invention, such as an antibody with a detectable label. Antibodies can be polyclonal, or more preferably, monoclonal. An intact antibody, or a fragment thereof (e.g., Fab or $F(ab')_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether a cell expresses a marker (e.g., an ERCC5 pathway member (e.g., ERCC5 or an ERCC5 variant)) of the present invention.

In one embodiment, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from epithelial cancer cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

In certain exemplary embodiments, kits for detecting the presence of a polypeptide or nucleic acid corresponding to a marker (e.g., an ERCC5 pathway member (e.g., ERCC5 or an ERCC5 variant)) in a biological sample (e.g. an epithelial cell-associated body fluid such as a saliva or blood sample or an epithelial tissue sample such as a cheek swab) are provided. Such kits can be used to determine if a subject is suffering from or is at increased risk of developing an epithelial cancer (such as, e.g., oral cancer). For example, the kit can comprise a labeled compound or agent capable of detecting a polypeptide or an mRNA encoding a polypeptide corresponding to a marker (e.g., an ERCC5 pathway member (e.g., ERCC5 or an ERCC5 variant)) in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for interpreting the results obtained using the kit.

For antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker (e.g., an ERCC5 pathway member (e.g., ERCC5 or an ERCC5 variant)) or (2) a pair of primers useful for amplifying a nucleic acid molecule corresponding to a marker (e.g., an ERCC5 pathway member (e.g., ERCC5 or an ERCC5 variant)). The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

The methods described herein can furthermore be utilized as diagnostic or prognostic assays to identify subjects having or at risk of developing a disease or disorder associated with aberrant expression or activity of a marker (e.g., an ERCC5 pathway member (e.g., ERCC5 or an ERCC5 variant)). For example, the assays described herein, such as the preceding diagnostic assays or the following assays, can be utilized to identify a subject having or at risk of developing a disorder associated with aberrant expression or activity of a marker (e.g., an ERCC5 pathway member (e.g., ERCC5 or an ERCC5 variant)), e.g., an epithelial premalignancy and/or an epithelial malignancy. Alternatively, the prognostic assays can be utilized to identify a subject having or at risk for developing an epithelial premalignancy and/or an epithelial malignancy. Thus, the present invention provides a method in which a test sample is obtained from a subject and a marker (e.g., an ERCC5 pathway member (e.g., ERCC5 or an ERCC5 variant)) polypeptide or nucleic acid (e.g., mRNA, genomic DNA) is detected, wherein the presence of the polypeptide or nucleic acid is diagnostic for a subject having or at risk of developing a disease or disorder associated with aberrant expression or activity of the polypeptide.

The prognostic assays described herein can be used to identify a subject having or at risk of developing epithelial premalignancies and/or epithelial malignancies, e.g., malignancies and/or premalignancies associated with epithelial cancers of the upper aerodigestive tract (e.g., oral cavity, larynx, pharynx, esophagus and the like), lung, cervix, colon and/or rectum. Furthermore, the prognostic assays described herein can be used to determine whether a subject can be administered an agent (e.g., an agonist, antagonist, peptidomimetic, protein, peptide, nucleic acid, small molecule, or other drug candidate) to treat an epithelial premalignancy and/or epithelial malignancy associated with one or more ERCC5 variants (e.g., an SNP such as rs751402) activity and/or expression. The present invention provides methods for determining whether a subject can be effectively treated with an agent for a disorder associated with aberrant expression or activity of a marker (e.g., an ERCC5 pathway member (e.g., ERCC5 or an ERCC5 variant)) in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

In certain exemplary embodiments screening assays for identifying modulators, i.e., candidate or test compounds or agents (e.g., antibodies, peptides, cyclic peptides, peptidomimetics, small molecules, small organic molecules, or other drugs) which have a stimulatory and/or inhibitory effect on ERCC5 or an ERCC5 variant and/or a stimulatory and/or inhibitory effect on one or more molecules downstream of ERCC5 or an ERCC5 variant in the ERCC5 pathway as described herein are provided.

As used herein, the term "small molecule" refers to a molecule, either naturally occurring or synthetic, that has a molecular weight of more than about 25 daltons and less than about 3000 daltons, usually less than about 2500 daltons, more usually less than about 2000 daltons, usually between about 100 to about 1000 daltons, more usually between about 200 to about 500 daltons.

In certain exemplary embodiments, assays for screening candidate or test compounds which bind to or modulate (e.g., stimulate and/or inhibit) one or more ERCC5 pathway members are provided. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.*, 12:145).

The candidate or test compound(s) described herein can be incorporated into pharmaceutical compositions suitable for administration. Such compositions typically comprise the nucleic acid molecule or protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In certain exemplary embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the candidate or test compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: A binder such as microcrystalline cellulose, gum tragacanth or gelatin; an excipient such as starch or lactose, a disintegrating agent such as alginic, acid, Primogel, or corn starch; a lubricant such as magnesium stearate or Sterotes; a glidant: such as colloidal silicon dioxide; a sweetening agent such as sucrose or saccharin; or a flavoring agent such as peppermint, methyl salicylate, or orange flavoring.

In one embodiment, the candidate or test compound(s) are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

Nasal compositions generally include nasal sprays and inhalants. Nasal sprays and inhalants can contain one or more active components and excipients such as preservatives, viscosity modifiers, emulsifiers, buffering agents and the like. Nasal sprays may be applied to the nasal cavity for local and/or systemic use. Nasal sprays may be dispensed by a non-pressurized dispenser suitable for delivery of a metered dose of the active component. Nasal inhalants are intended for delivery to the lungs by oral inhalation for local and/or systemic use. Nasal inhalants may be dispensed by a closed container system for delivery of a metered dose of one or more active components.

In one embodiment, nasal inhalants are used with an aerosol. This is accomplished by preparing an aqueous aerosol, liposomal preparation or solid particles containing the compound. A non-aqueous (e.g., fluorocarbon propellant) suspension could be used. Sonic nebulizers may be used to minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The candidate or test compound(s) can also be prepared in the form of suppositories (e.g., with conventional suppository bases such as cocoa butter and other glycerides) or retention enemas for rectal delivery.

In one embodiment, candidate or test compound(s) are prepared with carriers that will protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of candidate or test compound(s) can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and/or animal studies can be used in formulating a range of dosage for use in humans. The dosage typically will lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In certain exemplary embodiments, a method for treatment of cancer or a pre-cancerous condition includes the step of administering a therapeutically effective amount of an agent (e.g., one or more candidate or test compounds) which modulates (e.g., stimulates and/or inhibits), one or more ERCC5 pathway members to a subject. As defined herein, a therapeutically effective amount of agent (i.e., an effective dosage) ranges from about 0.001 to 30 mg/kg body weight, from about 0.01 to 25 mg/kg body weight, from about 0.1 to 20 mg/kg body weight, or from about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an inhibitor can include a single treatment or, in certain exemplary embodiments, can include a series of treatments. It will also be appreciated that the effective dosage of inhibitor used for treatment may increase or decrease over the course of a particular treatment. Changes in dosage may result from the results of diagnostic assays as described herein. The pharmaceutical compositions can be included in a container, pack, or dispenser together with instructions for administration.

In certain embodiments, monitoring the influence of agents (e.g., drugs, compounds) on the expression or activity of ERCC5 or an ERCC5 variant (e.g., the ability to modulate aberrant cell proliferation and/or premalignancy development) can be applied not only in basic drug screening, but also in clinical trials. For example, the effectiveness of an agent, as determined by a screening assay as described herein, to decrease ERCC5 or ERCC5 variant gene expression, protein levels or protein activity, can be monitored in clinical trials of subjects exhibiting increased ERCC5 or ERCC5 variant gene expression, protein levels, or protein activity. Alternatively, the effectiveness of an agent, as determined by a screening assay, to increase ERCC5 or ERCC5 variant gene expression, protein levels or protein activity, can be monitored in clinical trials of subjects exhibiting decreased ERCC5 or ERCC5 variant gene expression, protein levels, or protein activity. In such clinical trials, expression or activity of a ERCC5 or ERCC5 variant polypeptide, that of other polypeptide(s) that have been implicated in for example, a cellular proliferation disorder (e.g., one or more ERCC5 pathway members), can be used as a marker of the immune responsiveness of a particular cell.

For example, and not by way of limitation, genes, including those of ERCC5 or ERCC5 variant(s), that are modulated in cells by treatment with an agent (e.g., an antibody, compound, drug or small molecule) that modulates activity or expression of an ERCC5 or ERCC5 variant polypeptide (e.g., as identified in a screening assay described herein) can be identified. Thus, to study the effect of agents on aberrant cellular proliferation, for example, in a clinical trial, cells can be isolated and RNA prepared and analyzed for the levels of expression of an ERCC5 or ERCC5 variant gene and other genes implicated in the disorder. The levels of gene expression (i.e., a gene expression pattern) can be quantified by Northern blot analysis or RT-PCR, as described herein, or alternatively by measuring the amount of protein produced by one of the methods as described herein, or by measuring the levels of activity of an ERCC5 or ERCC5 variant gene or other genes. In this way, the gene expression pattern can serve as a marker, indicative of the physiological response of the cells to the agent. Accordingly, this response state may be determined before, and at various points during, treatment of the individual with the agent.

In certain exemplary embodiments, a method is provided for monitoring the effectiveness of treatment of a subject with an agent (e.g., an agonist, antagonist, antibody, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of ERCC5 or ERCC5 variant polypeptide or nucleic acid in the preadministration sample; (iii) obtaining one or more post-administration samples from the subject; (iv) detecting the level the of ERCC5 or ERCC5 variant polypeptide or nucleic acid in the post-administration samples; (v) comparing the level of ERCC5 or ERCC5 variant polypeptide or nucleic acid in the pre-administration sample with the level of ERCC5 or ERCC5 variant polypeptide or nucleic acid in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

Embodiments of the invention are directed to a first nucleic acid (e.g., a nucleic acid sequence encoding one or more ERCC5 or ERCC5 variant nucleic acid sequences (e.g., SNPs)) or polypeptide sequence (e.g., one or more ERCC5 or ERCC5 variant polypeptides) having a certain sequence identity or percent homology to a second nucleic acid or polypeptide sequence, respectively.

Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics*, 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov (1986) *Nucl. Acids Res.*, 14:6745. An exemplary implementation of this algorithm to determine percent identity of a sequence is provided by the Genetics Computer Group (Madison, Wis.) in the "BestFit" utility application. The default parameters for this method are described in the Wisconsin *Sequence Analysis Package Program Manual*, Version 8 (1995) (available from Genetics Computer Group, Madison, Wis.).

One method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the NCBI/NLM web site.

Alternatively, homology can be determined by hybridization of polynucleotides under conditions that form stable duplexes between homologous regions, followed by digestion with single-stranded-specific nuclease(s), and size determination of the digested fragments. Two DNA sequences, or two polypeptide sequences are "substantially homologous" to each other when the sequences exhibit at least about 80%-85%, at least about 85%-90%, at least about 90%-95%, or at least about 95%-98%, or at least about 99% or more sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *Molecular Cloning: A Laboratory Manual*, Second Edition, (1989) Cold Spring Harbor, N.Y.; *Nucleic Acid Hybridization: A Practical Approach*, editors B. D. Hames and S. J. Higgins, (1985) Oxford; Washington, D.C.; IRL Press.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization*, supra).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as varying wash conditions. The selection of a particular set of hybridization conditions is selected following standard methods in the art (see, for example, Sambrook et al., supra).

As used herein, the term "hybridizes under stringent conditions" is intended to describe conditions for hybridization and washing under which nucleotide sequences at least 60% identical to each other typically remain hybridized to each other. In one aspect, the conditions are such that sequences at least about 70%, at least about 80%, at least about 85% or 90%, at least about 95%, at least about 99% or more identical to each other typically remain hybridized to each other. Such stringent conditions are known to those skilled in the art and can be found in *Current Protocols in Molecular Biology*, John Wiley & Sons, NY (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50° C., at 55° C., or at 60° C. or 65° C.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, and accompanying claims.

EXAMPLE 1

Gene Environment Interaction Between ERCC5 and Tobacco in Oral Pre-Malignancies

Objective: to assess the role of genetic variation at ERCC5 during the early phases of oral carcinogenesis. ERCC5 is found on chromosome 13 (13q33) and it is involved in the regulation of DNA repair. Methods: 106 individuals with confirmed oral premalignancies (OPs) and 212 healthy controls were selected to participate in a nested case-control within the Health Professionals Follow Up Study (HPFS), a group of 55,000+ health professionals who are followed up regularly since 1986. Cases and controls provided information on smoking, alcohol use, diet, and demographics. They also volunteered to provide blood. After DNA extraction, PCR based genotyping methods were used to characterize among others the genotype rs751402 (exon 1, C/T, with 42% described heterozygosity). Results were analyzed using logistic regression in Stata 9.0. Results: Bivariate and multivariate statistics confirmed that tobacco and alcohol use increase the risk of OP where fruit consumption was associated with reduced risks. With regard to smokeless tobacco use, the odds ratio (OR) was 3.5, with a 95% confidence interval (C.I.) of 1.4-8.5 ($p<0.05$). The risk of premalignancy among homozygotes for ERCC5 rs751402 was increased by 89% (95% C.I.: 1.1-3.2) as compared with individuals who did not harbor the genotype. However multivariate stratified analysis revealed that ERCC5 rs751402-positive individuals had a 26-fold increase in their risk if the used tobacco (95% C.I.: 1.03-669.1). The statistical interaction was significant (OR=5.1, 95% C.I.: 1.9-13.8).

A strong gene environment interaction between ERCC5 and smokeless tobacco use was documented. This is the first report to describe an interaction between the genetics of DNA repair and the use of smokeless tobacco in oral carcinogenesis.

EXAMPLE II

Methods

Advanced PCR-based genotyping and subsequent bio-informatic analysis of data were obtained from 321 subjects that were either cases with epithelial premalignancies or cancer or controls (healthy individuals of similar age and gender with the cases) (FIG. 2). All participants provided a nucleic acid sample (blood) as well as longitudinal information on several personal characteristics which can be described as covariates or "risk factors." The genotyping result was then used in a conditional logistic regression model that examined main effects as well as statistical interactions while controlling for the statistical effects of several important and significant co-variates or risk factors such as tobacco use, alcohol drinking, body mass index, and several dietary variables. The results of the analysis indicated that gene ERCC5, which is involved in the DNA repair pathway, modifies the effect of tobacco use, particularly smokeless chewing tobacco.

Based on the identification of the DNA repair ERCC5 SNP associated with tobacco induced epithelial cancer, certain exemplary embodiments are directed to methods for identifying individuals who have an altered (i.e., increased or decreased) risk of developing tobacco induced epithelial cancers based on the presence of the ERCC5 rs751402 SNP, its encoded product, methods of identifying individuals who are more or less likely to respond to a treatment, methods of identifying tobacco using individuals who are more or less likely to respond to a behavioral or clinical or community intervention to stop cancer, methods of screening individuals to prevent them from using tobacco products due to their increased cancer risk, methods of screening for compounds useful in the treatment of a disorder associated with a variant gene/protein, compounds identified by these methods, methods of treating cancer mediated by a variant gene/protein, methods of using the novel SNP of the present invention for human identification and the like.

Study Design Overview

The inventor conducted a case-control study to evaluate certain biomarkers in the etiology of epithelial cancers and/or precancerous lesions such as leukoplakias, erythroplakias, mixed lesions and the like. The case-control design is a well-accepted methodology in epidemiology in identifying potential risk factors, especially when the disease entity is rare. Disease status and exposure assessment details for a number of exposures of interest such as smoking, smokeless tobacco use, frequency and amounts of alcohol consumption, type of alcohol, dietary assessment, and demographics were collected and analyzed. Cases consented to provide a nucleic acid sample (i.e., blood) for molecular analysis. DNA was extracted from blood and genotyped.

Blood was collected in tubes containing sodium ethylenediaminetetraacetic acid, chilled during the overnight courier transportation, centrifuged at 4° C., and aliquoted into plasma, erythrocytes, and buffy coat. Each component then was stored in −150° C. liquid nitrogen freezers. A large plasma quality control pool was created to monitor changes in plasma parameters with long-term storage and variability in laboratory assays. Repeat blood specimens from 40 men were obtained to calculate and correct for within-person variability. Buccal cell collection kits were sent to participants in the mail, and then centrifuged, processed and stored in the vapor phase of a liquid nitrogen freezer at −130° C.

Exposure Assessment

Information on the following tobacco use measures were gathered: Number of cigarettes per day smoked during years of active smoking (1-4, 5-14, 15-24, 25-34, 35-44, or 45+), preferred brand and type of cigarettes, ever use of chewing tobacco (>1/week), and current daily use of pipes or cigars. The questionnaire also asked about past smoking, how long ago the participant quit if he was a past smoker, and the average number of cigarettes smoked per day before age 15 years and in 5-year age intervals since then.

Information on the following alcohol consumption measures were gathered by the biennial HPFS questionnaires: number of alcoholic drinks per day or week consumed during years of active drinking, preferred type of beverage consumed per day or week. The database contains the above plus grams of alcohol; alcohol amount in grams is calculated with a standard formula that takes into account the alcoholic content in its type of beverage.

DNA Extraction and Genotyping

DNA extraction and genotyping was assessed at the Core genotyping facility of the Harvard Partners Center for Genotyping and Genomics (Website: hpcgg.org). DNA for genotyping was isolated from peripheral blood leukocytes. DNA extraction from peripheral blood leukocytes used standards methods (QIAamp Blood Kit, QIAGEN Inc., Chatsworth, Calif.).

The primary techniques for detecting specific polymorphisms was the Taqman allelic discrimination assays and matrix-assisted laser desorption ionization (MALDI-TOF) mass spectrometry using the Sequenom system. Samples of genomic DNA were subjected to standard polymerase chain reactions (PCR) to amplify genomic DNA flanking the target polymorphism. 2.5 ng genomic DNA (1.25 ng/µl in water) was amplified in a 5 µl reaction containing 0.1 U HotStar Taq polymerase and 1× HotStar Taq PCR Buffer (Qiagen Inc., Valencia, Calif.), 2.5 mM $MgCl_2$, 200 µM of each deoxynucleotide triphosphate (dNTPs) (USB, Cleveland, Ohio), 50 nM each PCR primer. Samples were incubated at 95° C. for 15 minutes followed by 45 cycles of 95° C. for 20 seconds, 56° C. for 30 seconds, 72° C. for 1 minute, followed by 3 minutes at 72° C. on a 384-well DNA Engine Tetrad (PTC225, MJResearch Inc., South San Francisco, Calif.). Excess dNTPs were then removed from the reaction by addition of 0.3 U shrimp alkaline phosphatase (SAP) (USB) in Thermosequenase RCTN Buffer (USB) at 37° C. for 20 minutes followed by 5 minutes at 85° C. Amplified PCR product was used as a template in a second, modified single-primer minisequencing reaction, whereby either single-base extension and chain termination or two to three base extensions occurs at the variant allele, as described above. Extension reactions contained 600 nM of extension primer, 50 µM d/dd-NTP in Thermosequenase RCTN Buffer and 0.126 U Thermosequenase (USB). Samples were at 94° C. for 2 minutes followed by 45 cycles of 94° C. for 5 seconds, 52° C. for 5 seconds, and 72° C. for 5 seconds. The minisequencing reaction was then desalted by addition of SpectroClean resin (Sequenome).

Using a nanoliter-plotting robot (SpectroPLOTTER, Sequenom), the purified minisequencing product was then spotted onto a chip (SpectroCHIPS, Sequenom) containing matrix pads. The matrix aided in desorption and ionization of the DNA. 384 individual DNA samples could be spotted on each chip. Chips were individually analyzed using the Brukker Bi-flex MALDI-TOF mass spectrometer (Sequenom).

With the MALDI-TOF mass spectrometer, which differentiates molecular mass, one could differentiate the SNP alleles by the different molecular weights of the allele specific products. Each spotted sample was analyzed using laser-mediated desorption and ionization of the minisequencing reaction extended oligonucleotide product. This resulted in acceleration of the extended oligonucleotide towards a detector. The velocity of the sample was proportional to oligonucleotide length. As a result, the time from laser-mediated desorption and ionization to detector signaling (time of flight—TOF) was directly correlated with oligonucleotide mass. The resulting spectra were converted to meaningful genotype data using SpectroTYPER-RT software (Sequenom), which interprets the spectral output based on information for expected allele-specific oligonucleotide lengths generated during the assay design phase. To reduce the potential for bias, laboratory technicians were blinded to case/control status. In addition, all steps involved were highly automated and were tracked using a laboratory management system with bar coding. Approximately 5% of repeated quality control samples were routinely added as blinded specimens, and were randomly nested in the sample, to be reviewed by a programmer.

Bioinformatics/Data Analysis

Two master data files were created in the data management phase, one for the general demographic and environmental risk factors and one for the genetic results. Both master data sets contained the same linking key, a unique identifier that made possible the merge of the two files into a single analytic file. The identity of the subjects had been masked and the analytic data file was anonymous to protect the confidentiality of study subjects.

Initial analysis examined distributions and descriptive statistics of the variant alleles, main risk factors (tobacco and alcohol use), and other cancer or precancer risk factors in cases and controls. Conditional logistic regression analyses was performed to assess the association between phenotypes and ERCC5 risk alleles. The matching factors were age (±5 years) and ethnicity. Covariates to be included in the conditional logistic regression model were those with clinical significance and those that satisfied the p<0.20 criterion in the bivariate analyses. The logit(p) was modeled as follows: logit $(p) = \beta 0 + \beta 1A + \beta 2B + \beta 3\Gamma + \beta 4\Delta \ldots + 62 \chi(\Lambda*B)$, where: $\beta 1 \ldots \beta \chi$ are the regression coefficients for factors which will be included in the model, A,B and the like denote the covariate names (age, years out of work, marital status, etc.). $\Lambda*B$ denote an interaction term between A, and B.

Adjusted Odds Ratios (i.e., ORA=eb) and confidence intervals (95% C.I.) were obtained from the logistic regression. Tests of association was performed using the Wald's method and the Likelihood Ratio Test (G=2{log LHA−log LH0}, where log LHA and log LH0 are the maximized likelihoods under the alternative and null hypotheses respectively). Evaluation of the degree of confounding and interaction, a priori concern and biologic plausibility influenced which were the variables selected to be included in the final model. Finally, goodness-of-fit of the model was assessed using the Hosmer-Lemeshow test.

To examine the contribution of tobacco to the association between genes and cancer and between genes and precancer, the conditional logistic regression analysis using the entire study sample was compared to an analysis excluding individuals who ever used tobacco. Also, every use of tobacco was entered into the final model to examine whether it mediates the association between gene and oral cancer or precancer.

REFERENCES

1. Sancar A (1996) "DNA excision repair," *Annu. Rev. Biochem.*, 65:43-81.
2. Hoeijmakers J H J (2001) "Genome maintenance mechanisms for preventing cancer," *Nature*, 411:366-374.
3. Lindhal T and Wood R D (1999) "Quality control by DNA repair," *Science*, 86:1897-1905.
4. Wilson D M and Thompson L H (1997) "Life without DNA repair," *Proc. Natl. Acad. Sci. U.S.A.*, 94:12754-12757.
5. Divine K K et al. (2001) "The XRCC1 399 glutamine allele is a risk factor for adenocarcinoma of the lung," *Mutat. Res.*, 461:273-278.
6. Kolodner R D and Marsischky G T (1999) "Eukaryotic DNA mismatch repair," *Curr. Opin. Genet. Dev.*, 9:86-96.
7. Harfe B D and Jinks-Robertson S (2000) "DNA mismatch repair and genetic instability," *Annu. Rev. Genet.*, 34:359-399.
8. Mol C D, Parikh S S, Putnam C D, Lo T P, and Tainer J A (1999) "DNA repair mechanisms for the recognition and removal of damaged DNA bases," *Annu. Rev. Biophys. Biomol. Struct.*, 28:101-128.
9. Zhou B B and Elledge S J (2000) "The DNA damage response: putting checkpoints in perspective," *Nature*, 408:433-439.
10. Khanna K K and Jackson S P (2001) "DNA double-strand breaks: signaling, repair, and the cancer connection," *Nature Genet.*, 27:247-254.
11. Kimball J (2006) *DNA Repair*. Biology Pages: Online textbook. Accessed Jul. 15, 2007 from http://users.rcn.com/jkimball.ma.ultranet/BiologyPages/D/DNArepair.html.
12. Rotman G and Shiloh Y (1998) "ATM: from gene to function," *Hum. Mol. Genet.*, 7:1555-1563.
13. Petrini J H (2000) "The Mre11 complex and ATM: collaborating to navigate S phase," *Curr. Opi. Cell Biol.*, 12:293-296.
14. Mudgett J S and MacInnes M A (1990) "Isolation of the functional human excision repair gene ERCC5 by intercosmid recombination," *Genomics*, 8:623-633.
15. O'Donovan A and Wood R d (1993) "Identical defects in DNA repair in xeroderma pigmentosum group G and rodent ERCC group 5," *Nature*, 363:185-188.
16. Scherly D, Nouspikel T, Corlet J, Ucla C, Bairoch A, and Clarkson S G (1993) "Complementation of the DNA repair defect in xeroderma pigmentosum group C cells by a human cDNA related to yeast RAD2," *Nature*, 363:182-185.
17. O'Donovan A, Davies A A, Moggs J G, West S C, and Wood R D (1994) "XPG endonuclease makes the 3' incision in human DNA nucleotide excision repair," *Nature*, 371:432-435.
18. Cloud K, Shen B, Strniste G, and Park M (1995) "XPG protein has a structure-specific endonuclease activity," *Mutat. Res.*, 347:55-60.
19. Evans E, Fellows J, Coffer A, and Wood R D (1997) "Open complex formation around a lesion during nucleotide excision repair provides a structure for cleavage by human XPG protein," *EMBO J.*, 16:625-638.
20. Hunting D J, Gowans B J, and Dresler S L (1991) "DNA polymerase delta mediates excision repair in growing cells damaged with ultraviolet radiation," *Biochem. Cell Biol.*, 69:303-308.
21. Coverley D, Kenny M K, Lane D P, and Wood R D (1992) "A role for the human single-stranded DNA binding protein HSSB/RPA in an early stage of nucleotide excision repair," *Nucl. Acids Res.*, 20:3873-3880.

What is claimed:

1. A method of diagnosing aerodigestive cancer in a human comprising the steps of:
   obtaining a biological sample from the human;
   detecting whether an ERCC5 single nucleotide polymorphism comprising SEQ ID NO:1 having a T at position 298 is present in the biological sample; and
   diagnosing the human with aerodigestive cancer if the human is homozygous for the ERCC5 single nucleotide polymorphism comprising SEQ ID NO:1 having a T at position 298.

2. The method of claim 1, wherein the biological sample is selected from the group consisting of a fluid sample, a tissue sample and a biopsy sample.

3. The method of claim 1, wherein the biological sample is selected from the group consisting of blood, cheek cells and saliva.

4. The method of claim 1, wherein the epithelial cancer is selected from the group consisting of oral cancer, laryngeal cancer, pharyngeal cancer, esophageal cancer, stomach cancer, lung cancer, cervical cancer, penile cancer, colon cancer and rectal cancer.

5. The method of claim 1, wherein the individual drinks alcohol, smokes tobacco or chews tobacco.

6. A method of diagnosing an aerodigestive premalignancy in a human comprising the steps of:
   obtaining a biological sample from the human;
   detecting whether an ERCC5 single nucleotide polymorphism comprising SEQ ID NO:1 having a T at position 298 is present in the biological sample; and
   diagnosing the human with an aerodigestive premalignancy if the human is homozygous for the ERCC5 single nucleotide polymorphism comprising SEQ ID NO:1 having a T at position 298.

7. The method of claim 6, wherein the biological sample is selected from the group consisting of a fluid sample, a tissue sample and a biopsy sample.

8. The method of claim 6, wherein the biological sample comprises a sample selected from the group consisting of blood, cheek cells and saliva.

9. The method of claim 6, wherein the epithelial premalignancy is selected from the group consisting of oral premalignancy, laryngeal premalignancy, pharyngeal premalignancy, esophageal premalignancy, stomach premalignancy, lung premalignancy, cervical premalignancy, penile premalignancy, colon premalignancy and rectal premalignancy.

10. The method of claim 6, wherein the individual drinks alcohol, smokes tobacco or chews tobacco.

11. A method of identifying a human at risk for developing an epithelial cancer comprising the steps of:
    obtaining a biological sample from the human;
    detecting whether an ERCC5 single nucleotide polymorphism comprising SEQ ID NO:1 having a T at position 298 is present in the biological sample; and
    identifying the human as being at risk for developing aerodigestive cancer if the human is homozygous for the ERCC5 single nucleotide polymorphism comprising SEQ ID NO:1 having a T at position 298.

12. The method of claim 11, wherein the biological sample is selected from the group consisting of a fluid sample, a tissue sample and a biopsy sample.

13. The method of claim 11, wherein the biological sample comprises a sample selected from the group consisting of blood, cheek cells and saliva.

14. The method of claim 11, wherein the epithelial cancer is selected from the group consisting of oral cancer, laryngeal cancer, pharyngeal cancer, esophageal cancer, stomach cancer, lung cancer, cervical cancer, penile cancer, colon cancer and rectal cancer.

15. The method of claim 11, wherein the individual drinks alcohol, smokes tobacco or chews tobacco.

16. method of detecting epithelial cancer in a biological sample comprising the steps of:
    obtaining a human biological sample; and
    detecting whether an ERCC5 single nucleotide polymorphism comprising SEQ ID NO:1 having a T at position 298 is present in the biological sample, and detecting aerodigestive cancer if the biological sample is homozygous for the ERCC5 single nucleotide polymorphism comprising SEQ ID NO:1 having a T at position 298.

17. A method of detecting an epithelial premalignancy in biological sample comprising the steps of:
    obtaining a human biological sample; and
    detecting whether an ERCC5 single nucleotide polymorphism comprising SEQ ID NO:1 having a T at position 298 is present in the biological sample, and detecting aerodigestive premalignancy if the biological sample is homozygous for the ERCC5 single nucleotide polymorphism comprising SEQ ID NO:1 having a T at position 298.

18. A method of screening a human at risk for developing an epithelial cancer comprising the steps of:
    obtaining a biological sample from the human;
    identifying the ERCC5 genotype of the human;
    obtaining tobacco exposure information for the human; and
    determining the human is at risk for developing an epithelial cancer if the human is homozygous for T at position 298 of SEQ ID NO:1 and if the individual is exposed to tobacco.

19. A method of diagnosing aerodigestive cancer in a human comprising the steps of:
    assaying whether an ERCC5 single nucleotide polymorphism comprising SEQ ID NO:1 having a T at position 298 is present in a biological sample from a human; and
    diagnosing the human with aerodigestive cancer if the human is homozygous for the ERCC5 single nucleotide polymorphism comprising SEQ ID NO:1 having a T at position 298.

20. The method of claim 19, wherein the biological sample is selected from the group consisting of a fluid sample, a tissue sample and a biopsy sample.

21. The method of claim 19, wherein the biological sample is selected from the group consisting of blood, cheek cells and saliva.

22. The method of claim 19, wherein the aerodigestive cancer is oral cancer, laryngeal cancer, pharyngeal cancer, or esophageal cancer.

23. The method of claim 19, wherein the individual drinks alcohol, smokes tobacco or chews tobacco.

24. A method of diagnosing an aerodigestive premalignancy in a human comprising the steps of:
    assaying whether an ERCC5 single nucleotide polymorphism comprising SEQ ID NO:1 having a T at position 298 is present in a biological sample from a human; and
    diagnosing the human with an aerodigestive premalignancy if the human is homozygous for the ERCC5 single nucleotide polymorphism comprising SEQ ID NO:1 having a T at position 298.

25. The method of claim 24, wherein the biological sample is selected from the group consisting of a fluid sample, a tissue sample and a biopsy sample.

26. The method of claim 24, wherein the biological sample comprises a sample selected from the group consisting of blood, cheek cells and saliva.

27. The method of claim 24, wherein the aerodigestive premalignancy is oral premalignancy, laryngeal premalignancy, pharyngeal premalignancy, or esophageal premalignancy.

28. The method of claim 24, wherein the individual drinks alcohol, smokes tobacco or chews tobacco.

29. A method of identifying a human at risk for developing an aerodigestive cancer comprising the steps of: assaying whether an ERCC5 single nucleotide polymorphism comprising SEQ ID NO:1 having a T at position 298 is present in a biological sample from the human; and identifying the human as being at risk for developing aerodigestive cancer if the human is homozygous for the ERCC5 single nucleotide polymorphism comprising SEQ ID NO:1 having a T at position 298.

30. method of claim 29, wherein the biological sample is selected from the group consisting of a fluid sample, a tissue sample and a biopsy sample.

31. The method of claim 29, wherein the biological sample comprises a sample selected from the group consisting of blood, cheek cells and saliva.

32. The method of claim 29, wherein the aerodigestive cancer is oral cancer, laryngeal cancer, pharyngeal cancer, or esophageal cancer.

33. The method of claim 29, wherein the individual drinks alcohol, smokes tobacco or chews tobacco.

34. A method of detecting aerodigestive cancer in a biological sample from a human comprising the steps of:
    assaying whether an ERCC5 single nucleotide polymorphism comprising SEQ ID NO:1 having a T at position 298 is present in the biological sample, and detecting aerodigestive cancer if the biological sample is homozygous for the ERCC5 single nucleotide polymorphism comprising SEQ ID NO:1 having a T at position 298.

35. A method of detecting an aerodigestive premalignancy in a biological sample from a human comprising the steps of:
    assaying whether an ERCC5 single nucleotide polymorphism comprising SEQ ID NO:1 having a T at position 298 is present in the biological sample, and detecting aerodigestive premalignancy if the biological sample is homozygous for the ERCC5 single nucleotide polymorphism comprising SEQ ID N0:1 having a T at position 298.

36. A method of screening a human at risk for developing an aerodigestive cancer comprising the steps of:
    assaying the ERCC5 genotype of the human from a biological sample from the human;
    obtaining tobacco exposure information for the human; and
    determining the human is at risk for developing an aerodigestive cancer if the human is homozygous for T at position 298 of SEQ ID NO:1 and if the individual is exposed to tobacco.

* * * * *